(12) United States Patent
Lampo

(10) Patent No.: US 11,289,186 B2
(45) Date of Patent: *Mar. 29, 2022

(54) PERSONALIZED IMAGE-BASED GUIDANCE FOR ENERGY-BASED THERAPEUTIC DEVICES

(71) Applicant: DJO, LLC, Lewisville, TX (US)

(72) Inventor: Pierre-Yves Lampo, Bretigny-sur-Morrens (CH)

(73) Assignee: DJO, LLC, Lewisville, TX (US)

( * ) Notice: Subject to any disclaimer, the term of this patent is extended or adjusted under 35 U.S.C. 154(b) by 252 days.

This patent is subject to a terminal disclaimer.

(21) Appl. No.: 16/564,980

(22) Filed: Sep. 9, 2019

(65) Prior Publication Data

US 2020/0075171 A1 Mar. 5, 2020

Related U.S. Application Data

(63) Continuation of application No. 15/851,404, filed on Dec. 21, 2017, now Pat. No. 10,410,751, which is a (Continued)

(51) Int. Cl.
*G16H 20/40* (2018.01)
*G16H 50/70* (2018.01)
*G16H 20/30* (2018.01)
*G16H 70/00* (2018.01)
*G16H 50/50* (2018.01)
(Continued)

(52) U.S. Cl.
CPC ............... *G16H 20/40* (2018.01); *A61N 5/06* (2013.01); *G16H 20/30* (2018.01); *G16H 30/20* (2018.01); *G16H 50/50* (2018.01); *G16H 50/70* (2018.01); *G16H 70/00* (2018.01); *A61B 2034/101* (2016.02); *A61B 2034/107* (2016.02); *A61N 1/36031* (2017.08); *A61N 1/37247* (2013.01); *A61N 7/00* (2013.01); *A61N 2005/0626* (2013.01); *A61N 2005/0643* (2013.01)

(58) Field of Classification Search
None
See application file for complete search history.

(56) References Cited

U.S. PATENT DOCUMENTS 6,622,048 B1 9/2003 Mann
9,852,262 B2 12/2017 Lampo
(Continued)

FOREIGN PATENT DOCUMENTS

CA 2827501 8/2012
CN 1522672 8/2004
(Continued)

OTHER PUBLICATIONS

International Search Report and Written Opinion dated Jul. 18, 2014 for PCT/US2014/020583.
(Continued)

*Primary Examiner* — Ankit D Tejani
(74) *Attorney, Agent, or Firm* — Knobbe Martens Olson & Bear LLP

(57) ABSTRACT

Systems and methods are provided for determining the placement of energy-delivery nodes of an energy-based therapeutic device. In one aspect, recommended placement locations are customized by analyzing an image or video of the user and may be superimposed on an image corresponding to an affected body part.

14 Claims, 11 Drawing Sheets

Related U.S. Application Data continuation of application No. 14/197,572, filed on Mar. 5, 2014, now Pat. No. 9,852,262.

(60) Provisional application No. 61/790,863, filed on Mar. 15, 2013.

(51) Int. Cl.
*G16H 30/20* (2018.01)
*A61N 5/06* (2006.01)
*A61N 1/372* (2006.01)
*A61N 7/00* (2006.01)
*A61B 34/10* (2016.01)
*A61N 1/36* (2006.01)

(56) References Cited

U.S. PATENT DOCUMENTS

| | | |
|---|---|---|
| 10,410,751 B2 | 9/2019 | Lampo |
| 2008/0281189 A1 | 11/2008 | Komuro et al. |
| 2009/0030286 A1 | 1/2009 | Amitai |
| 2009/0198511 A1 | 8/2009 | Boehlke |
| 2009/0306746 A1 | 12/2009 | Blischak |
| 2010/0049037 A1 | 2/2010 | Pinter et al. |
| 2010/0249627 A1 | 9/2010 | Zhang |
| 2011/0015504 A1 | 1/2011 | Yoo |
| 2011/0106213 A1 | 5/2011 | Davis |
| 2012/0172674 A1 | 7/2012 | Welz |
| 2012/0183940 A1 | 7/2012 | Aragones |
| 2013/0060315 A1 | 3/2013 | Elghazzawi et al. |

FOREIGN PATENT DOCUMENTS

| | | |
|---|---|---|
| CN | 2696233 Y | 4/2005 |
| CN | 101511296 | 8/2009 |
| CN | 102421386 | 4/2012 |
| CN | 102740791 | 10/2012 |
| CN | 102933153 | 2/2013 |
| EP | 1 219 320 | 7/2002 |
| EP | 1 930 832 | 6/2008 |
| WO | WO 10/131131 | 11/2001 |
| WO | WO 08/032234 | 3/2008 |
| WO | WO 11/047387 | 4/2011 |
| WO | WO 11/049802 | 4/2011 |
| WO | WO 12/119649 | 9/2012 |
| WO | WO 13/012869 | 1/2013 |
| WO | WO 13/032710 | 3/2013 |

OTHER PUBLICATIONS

Extended European Search Report dated Jul. 21, 2016 in related European application No. 14768928.5.

PERSONALIZED IMAGE-BASED GUIDANCE FOR ENERGY-BASED THERAPEUTIC DEVICES

CROSS REFERENCE TO RELATED APPLICATIONS

This application is a continuation of U.S. application Ser. No. 15/851,404, filed Dec. 21, 2017, and scheduled to issue on Sep. 10, 2019, as U.S. Pat. No. 10,410,751, which is a continuation of U.S. application Ser. No. 14/197,572, filed Mar. 5, 2014, which issued on Dec. 26, 2017, as U.S. Pat. No. 9,852,262, which claims priority under 35 U.S.C. § 119(e) to U.S. Provisional Patent Application No. 61/790,863, filed Mar. 15, 2013, entitled "PERSONALIZED IMAGE-BASED GUIDANCE FOR ENERGY-BASED THERAPEUTIC DEVICES." Each of the above-identified applications is hereby incorporated by reference in its entirety. Any and all applications for which a foreign or domestic priority claim is identified in the Application Data Sheet as filed with the present application are hereby incorporated by reference under 37 C.F.R. § 1.57.

BACKGROUND

Technological Field

This application relates generally to the use and application of electrotherapy devices. More particularly, systems and methods for image-based guidance in the application of such devices are disclosed.

Description of the Related Art

Energy-based therapeutic devices rely on the application of energy to an external region of a patient's body in order to provide localized treatment or relief to a condition affecting the region. Treatment can be provided using any combination of one or more of a number of energy sources, including low-voltage electricity, magnetic waves, radio waves, shockwaves, microwaves, radiofrequency, laser, heat waves, ultrasound, light waves, and the like. The energy is delivered to a desired region of the patient via an externally applied energy transmission member or node (e.g., electrodes, pads, transducers, or patches) attached to the device. For example, electrotherapy includes the application of electrical or electromagnetic stimulation to a particular part of the body for medical purposes. Electrotherapy treatment is widely used by doctors, therapists, athletes, trainers, and coaches for a variety of medical applications, including muscle stimulation, neurological diseases, pain management, treatment of neuromuscular dysfunction, improving the range of joint mobility, tissue repair, treatment for acute and chronic edema, improving peripheral blood flow, iontophoresis, preventing thrombosis post-surgery, and urine and fecal incontinence among other ailments. Electrotherapy treatments generally involve the use of an electro-stimulation device to generate electrical pulses which are delivered to the treatment site via electrodes placed in close proximity to the site. The electrodes are available in an assortment of practical and useful shapes and sizes, and may be applied to the body by being planted on the surface of the skin, just beneath the skin, or deep into tissue, depending on the nature of the injury or the particular treatment sought.

Regardless of the nature of the injury or the treatment, proper application of the energy-based therapeutic device is essential to the effectiveness of the treatment to the desired site. Existing guidance on the placement of devices consist of "one-size fits all" leaflets or electronic publications that are typically not at all customized to the nature of the injury, the particular treatment sought, and/or the physiology, health, and anatomy of the particular user.

Therefore it would be advantageous to provide a system and method for providing personalized, image-based guidance to patients in the application and use of energy-based therapeutic devices.

SUMMARY

The devices of the present disclosure have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description," one will understand how the features of this invention provide several advantages over current designs.

Disclosed herein are systems and methods for determining the placement of energy-delivery nodes of an energy-based therapeutic device. As used herein, an energy-delivery node refers to any suitable non-invasive means for externally applying energy from an energy-based device to a particular site on a patient. Examples of energy-delivery nodes include electrodes, ultrasound transducers, hot-and-cold pads, shockwave delivery nodes, and other conductive transducers, pads, patches and the like used to provide external stimulation or therapy to a site on a patient. In general, the systems and methods described herein remotely provide customized guidance to a user on the placement of electrodes or other energy-delivery nodes of an energy-based therapeutic device for treating a variety of physical conditions. In one example, recommended placement locations are customized by analyzing an image or video of the user and may be superimposed on an image corresponding to an affected body part. More specifically, embodiments of the systems and methods described herein can receive an input signal from processing circuitry, such as at least one processor, that includes user-specific information (such as an image, video, or other media representative of an affected body part, a user's medical history, an indication of the location and nature of the injury, condition, and other information). The input signal is processed using computational signal processing techniques to analyze the injury or condition. Systems and methods described herein can then provide, via a data port that is in communication with the processing circuitry, image-based guidance including an annotated virtual reality image on the proper placement of electrodes or other energy-delivery nodes to treat the injury or condition. In some implementations, the guidance also includes a recommendation for a non-invasive energy-based therapeutic device and recommendations on optimal sizes for electrodes or other energy-delivery nodes. The placement positions may be superimposed on the image or video provided by a user. The systems and methods described herein can be adapted and applied to other therapies such as ultrasound therapies, shockwaves, temperature-based treatment therapies, and any suitable combination thereof. These therapies can be used to treat a variety of physical conditions, such as musculoskeletal disorders, neurological disorders, soft-tissue disorders, pain, swelling, muscle fatigue, spinal conditions involving nerve root compression, muscle spasms, radiculopathy, discogenic conditions, and others.

According to one aspect, a method for providing guidance on the use of a non-invasive energy-based therapeutic device for treating a physical condition includes receiving an image or video of an affected body part of a subject, and providing customized guidance regarding the non-invasive placement of electrodes or other energy-delivery nodes on the user while analyzing the image or video. In general, the method for providing guidance on use of a non-invasive energy-based therapeutic device for treating one or more physical conditions includes receiving, by one or more computers, first media including a first image or a first video corresponding to a body part of a subject having a physical condition in need of non-invasive energy-based therapy. The first media can be received from any suitable user device, including but not limited to cameras, a smartphone, other mobile phone, or other data transmitting devices. In some implementations (as described in detail below), the one or more computers include processing circuitry (such as a processor) located within the same user device (e.g., a smartphone including a stand-alone application) that analyzes the first media and provides electrode (or other energy-delivery node) placement guidance. The one or more computers may be in communication with a node placement database (DB) and a pathology database and may analyze the first media based at least in part on information from the pathology database and information specific to the subject to characterize the physical condition of the body part. The one or more computers may further select a non-invasive energy-based therapeutic device from a node placement database based on analyzing the first media, where the non-invasive energy-based therapeutic device may administer a therapy using one or more electrodes or other energy-delivery nodes.

Additionally, the one or more computers may determine a placement position for each of the one or more electrodes or other energy-delivery nodes based on the analysis of the first media. In some implementations, the one or more computers provide a second media that includes the determined placement position for each of the one or more electrodes or other energy-delivery nodes. The second media may include a second image or a second video illustrative of the placement position of each of the electrodes (or other energy-delivery nodes) in order to provide guidance for treating the physical condition. In some implementations, the media includes a two-dimensional, a three-dimensional image, an image or video generated or composed based at least in part on the information specific to the subject, an actual image or video taken of the body part of the subject and/or a real-time image or video. The media may be a digital photograph. The media may include additional information regarding the physical condition and analyzing the media includes analyzing the first image or first video in conjunction with the additional information. The additional information may include a history of the physical condition, symptoms of the physical condition, demographic information about the subject, a preferred non-invasive energy-based therapeutic device, health of the subject, and any suitable combination thereof. The first media may also include a graphical annotation of a location of the injury.

The placement database may include a plurality of non-invasive energy-based therapeutic devices, including devices from different vendors. The pathology database may include anatomical libraries and/or decrypted pathologies. In some implementations, analyzing the media includes comparing the media to the pathology database, analyzing the media using image processing software, analyzing the media using augmented reality algorithms and/or extrapolating the first media using the pathology database. The physical condition may include a musculoskeletal disorder, a neurological disorder, a soft-tissue disorder, pain, swelling, muscle fatigue, a combination of these conditions, or another physical condition. The information specific to the subject may be obtained from a user profile database. The user profile database may include a plurality of user-expressed preferences, such as but not limited to preferences based on cost of treatment and/or preferences based on products from a specific vendor.

Determining the placement position can include determining the placement position based on user-specific information obtained from the user profile database. Selecting the non-invasive energy-based therapeutic device may include receiving information regarding a particular device associated with the subject or comparing the particular device with a plurality of available devices to determine a closest matching non-invasive energy-based therapeutic device for the particular application and condition. Selecting the non-invasive energy-based therapeutic device may also include selecting the closest matching device as the non-invasive energy-based therapeutic device. In some implementations, the method of providing guidance further includes determining a pad size for each of the one or more electrodes or other energy-delivery nodes. In these implementations, providing the second media includes providing an indication of the pad size for each of the electrodes or other energy-delivery nodes.

Methods described herein may provide guidance information for the use of the non-invasive energy-based therapeutic device based on an analysis of user-specific information relevant to the condition to be treated. The guidance can be provided as a second media derived or determined based on the user information, such as by providing an annotated image that is indicative of the guidance. Providing the guidance can include superimposing an indicator of the placement location for each of the one or more electrodes or other energy-delivery nodes on the first image or the first video or transmitting the second media to the user device connected to a network. Providing the second media may also include providing access to an on-line resource, access to commercial tools, references to illustrative videos, projected benefits of using the selected non-invasive energy-based therapeutic device and/or a flowchart to provide further placement position guidance on the use of the non-invasive energy-based therapeutic device. In some implementations, providing the second media includes sending the second media to a user device, updating a user profile associated with the subject to include a reference to the second media, and/or providing the second media for display on the user device. Receiving the first media may include receiving the first media from a user device. A user device may be a smartphone, a camera, a tablet computer, a non-invasive energy-based therapeutic device, and/or a suitable combination thereof.

In some implementations, providing the second media includes providing to a user device the second media including a placement position for each of the one or more electrodes or other energy-delivery nodes and computer readable instructions for annotating the first media to visually indicate the placement position for each of the electrodes or other energy-delivery nodes on the user device. The computer readable instructions may include instructions for graphically annotating the first media. In some implementations, the method further includes annotating by the user device the first media to include the placement position for each of the one or more electrodes or other energy-delivery nodes based on the instructions.

According to another aspect, a system for providing guidance on use of a non-invasive energy-based therapeutic device for treating a physical condition includes one or more processors in communication with one or more storage devices storing at least a placement database and a pathology database. The one or more processors may be associated with at least one communications circuitry coupled to a network for receiving communications over the network and may be configured to receive first media including a first image or a first video corresponding to a body part of a subject having a physical condition in need of treatment or therapy. The one or more processors may be additionally configured to analyze the first media based at least in part on information from the pathology database and information specific to the subject to characterize the physical condition of the body part. The one or more processors may be further configured to select, based on the analysis, a non-invasive energy-based therapeutic device from the placement database. The one or more processors may be configured to receive an indication of a preferred non-invasive energy-based therapeutic device for the subject. In some implementations, the placement database includes a plurality of non-invasive energy-based therapeutic devices. The non-invasive energy-based therapeutic device may administer a therapy using one or more electrodes or other energy-delivery nodes.

The one or more processors may be configured to determine a placement position for each of the one or more electrodes or other energy-delivery nodes based on the analysis of the first media. In some implementations, the system includes at least one communications circuitry configured to provide second media that includes the placement position for each of the one or more electrodes or other energy-delivery nodes. The second media may include a second image or a second video illustrative of the placement position of each of the electrodes or other energy-delivery nodes in order to provide guidance for treating the physical condition. In some implementations, media includes a two-dimensional image or video, a three-dimensional image or video, an image or video generated or composed based at least in part on the information specific to the subject, an actual image or video taken of the body part of the subject, a graphical annotation of a location of the injury and/or a real-time image. The media may be a digital photograph. The media may also include additional information regarding the physical condition and analyzing the first media may include analyzing the first image or first video in conjunction with the additional information. The additional information may include a history of the physical condition, symptoms of the physical condition, demographic information about the subject, a preferred non-invasive energy-based therapeutic device, health of the subject, and/or any suitable combination thereof.

In some implementations, the placement database includes devices from different vendors. The pathology database may include anatomical libraries and/or decrypted pathologies. The one or more processors may be configured to analyze the media by comparing the media (for example, the first media) to the pathology database, by using image processing software, by using augmented reality algorithms, or by extrapolating the first media using the pathology database. Or tools and methods to analyze the media may also be suitable. The physical condition may include a musculoskeletal disorder, a neurological disorder, a soft-tissue disorder, pain, swelling, muscle fatigue, a combination of these conditions, or another condition. In some implementations, the information specific to the subject is obtained from a user profile database. The user profile database may include a plurality of user-expressed preferences. Furthermore, the user-expressed preferences can include preferences based on cost of treatment and/or preferences based on products from a specific vendor.

The one or more processors can be configured to determine the placement position based on the user-specific information from the user profile database. The one or more processors may be configured to select the non-invasive energy-based therapeutic device by receiving information regarding a particular device associated with the subject. The particular device associated with the subject may be a device the subject has previously used, a device the subject prefers, a device a clinician or doctor has recommend for use by the subject, or another device. The one or more processors may compare the particular device with the plurality of available devices to determine a closest matching non-invasive energy-based therapeutic device. In some implementations, the one or more processors select the closest matching device as the non-invasive energy-based therapeutic device. In some implementations, the system further includes one or more processors configured to determine a pad size for each of the one or more electrodes or other energy-delivery nodes. At least one communications circuitry may be configured to provide the second media by providing an indication of the pad size for each of the electrodes or other energy-delivery nodes.

Systems described herein can provide guidance information for the use of the non-invasive energy-based therapeutic device based on an analysis of user-specific information relevant to the condition to be treated. The guidance can be provided as a second media derived or determined based on the user information, such as by providing an annotated image that is indicative of the guidance. At least one communications circuitry may be configured to provide the second media by providing an indication of the pad size for each of the electrodes or other energy-delivery nodes; superimposing an indicator of the placement location for each of the one or more electrodes or other energy-delivery nodes on the first image or the first video; transmitting the second media to the user device connected to the network; updating a user profile associated with the subject to include a reference to the second media; providing the second media for display on the user device; or any suitable combination of these. The second media may further include access to an on-line resource, access to commercial tools, a flowchart to provide further placement position guidance on the use of the non-invasive energy-based therapeutic device and/or projected benefits of using the selected device. In some implementations, the one or more processors are configured to receive the first media by receiving the first media from a user device. The user device may be a smartphone, a camera, a tablet computer, a non-invasive energy-based therapeutic device, and/or a suitable combination thereof.

According to another aspect, a computer-implemented method for identifying one or more placement locations for one or more electrodes or other energy-delivery nodes may include sending by a user device, first media including a first image or a first video depicting an external surface of a body part of a subject having a physical condition and information specific to the subject. The method may further include receiving from one or more computers, second media including a placement position for each of one or more electrodes or other energy-delivery nodes of a non-invasive energy-based therapeutic device selected based on the information specific to the subject and computer-readable instructions for annotating the first media to visually indicate the placement position for each of the electrodes or other energy-delivery nodes on the user device. In some implementations, one or more computers include a computer system including a communications port and computer processing circuitry in communication with at least one non-transitory computer readable medium storing a placement database configured to store a plurality of placement configurations for electrodes or other energy-delivery nodes, and optionally a pathology database. The one or more computers may include one or more computers in distributed architecture and/or one more computers in a cloud computing environment. Additionally, the method can also include annotating on the user device the first media to include the placement position for each of the one or more electrodes or other energy-delivery nodes based on instructions from the second media and communicating on an output port the annotated media to a user.

According to another aspect, a system for receiving guidance on use of a non-invasive energy-based therapeutic device for treating a physical condition includes one or more processors being associated with at least one communications circuitry coupled to a network for providing communications over the network. The one or more processors can be configured to send first media including a first image or a first video corresponding to a body part of a subject having a physical condition and information specific to the subject. At least one communications circuitry may be configured to receive a second media including a placement position for each of one or more electrodes or other energy-delivery nodes of a non-invasive energy-based therapeutic device selected based on the information specific to the subject and instructions for annotating the first media to visually indicate the placement position for each of the electrodes or other energy-delivery nodes on the user device. The one or more processors may be additionally configured to graphically annotate on the user device the first media to include the placement position for each of the one or more electrodes or other energy-delivery nodes based on instructions from the second media.

In one aspect of the present disclosure, a method for identifying one or more placement locations for one or more energy-delivery nodes of an energy-based therapeutic device is provided. The method includes receiving, by a computer system, a first media including a first image or a first video depicting an external surface of a body part of a subject having a physical condition in need of energy-based therapy. The computer system includes a processor in communication with at least one non-transitory computer readable medium storing a node placement database configured to store a plurality of node placement configurations. The method further includes analyzing, by the computer system, the first media to characterize the physical condition of the body part. The method includes determining a placement position for each of the one or more energy-delivery nodes of the energy-based therapeutic device based on the characterized physical condition, the placement position selected from one of the plurality of node placement configurations stored in the node placement database. The method also includes providing a second media including the determined placement position for each of the one or more energy-delivery nodes, the second media including a second image or a second video depicting the determined placement position of each of the one or more energy-delivery nodes in relation to the body part depicted in the first media.

In some implementations, the method further includes receiving, by the computer system, an indication of an energy-based therapeutic device preferred by the subject. Determining the placement position for each of the one or more energy-delivery nodes can include selecting a placement position from a plurality of node placement configurations relating to the preferred energy-based therapeutic device.

In another aspect of the present disclosure, a system for determining one or more placement locations for one or more energy-delivery nodes of an energy-based therapeutic device is provided. The system includes a camera configured to capture a plurality of images or videos depicting an external surface of a body part of a subject having a physical condition in need of energy-based therapy. The system also includes a pre-established media library storing a plurality of node placement configurations. The system further includes a placement-position processor configured to process the plurality of images or videos using the pre-established media library to determine a placement position for each of the one or more energy-delivery nodes of the energy-based therapeutic device. The system also includes a display configured to indicate the one or more determined placement positions to a user.

BRIEF DESCRIPTION OF THE DRAWINGS

These and other features, aspects, and advantages of the present invention will now be described in connection with embodiments of the present invention, in reference to the accompanying drawings. The illustrated embodiments, however, are merely examples and are not intended to limit the invention.

DETAILED DESCRIPTION

Any feature or combination of features described herein are included within the scope of the present disclosure provided that the features included in any such combination are not mutually inconsistent as will be apparent from the context, this description, and the knowledge of one skilled in the art. In addition, any feature or combination of features may be specifically excluded from any embodiment of the present disclosure. For purposes of summarizing the present disclosure, certain aspects, advantages, and novel features of the present disclosure are described herein. Of course, it is to be understood that not necessarily all such aspects, advantages, or features will be present in any particular embodiment of the present disclosure.

In reference to the disclosure herein, for purposes of convenience and clarity only, directional terms, such as, top, bottom, left, right, up, down, upper, lower, over, above, below, beneath, rear, and front, may be used. Such directional terms should not be construed to limit the scope of the invention in any manner. It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the invention.

Described herein are systems and methods that provide customized guidance for the treatment of various physical conditions, particularly for the treatment of physical conditions using a non-invasive energy-based therapeutic device. To provide an overall understanding, certain illustrative implementations will now be described, including systems and methods that provide visual guidance on the proper placement of one or more electrodes of a non-invasive electrotherapy device for the treatment of a variety of physical conditions. However, it will be understood by one of ordinary skill in the art that the systems and methods described herein can be applied to other types of energy-based therapeutic devices without departing from the scope hereof. In particular, the systems and methods described herein can be applied to provide guidance on the placement of one or more energy-delivery nodes for any energy-based therapeutic device. For example, the systems and methods described herein can be applied to hot or cold pain relieving gels, ultrasound devices, laser-based devices, shockwave therapy devices, cryotherapy devices, and the like, with respect to the treatment of one or more of any number of physical conditions and therapeutic purposes, including, for example, pain management, orthopedic rehabilitation, physical therapy, fitness and sport performance enhancement, and the like.

Figure 1A:
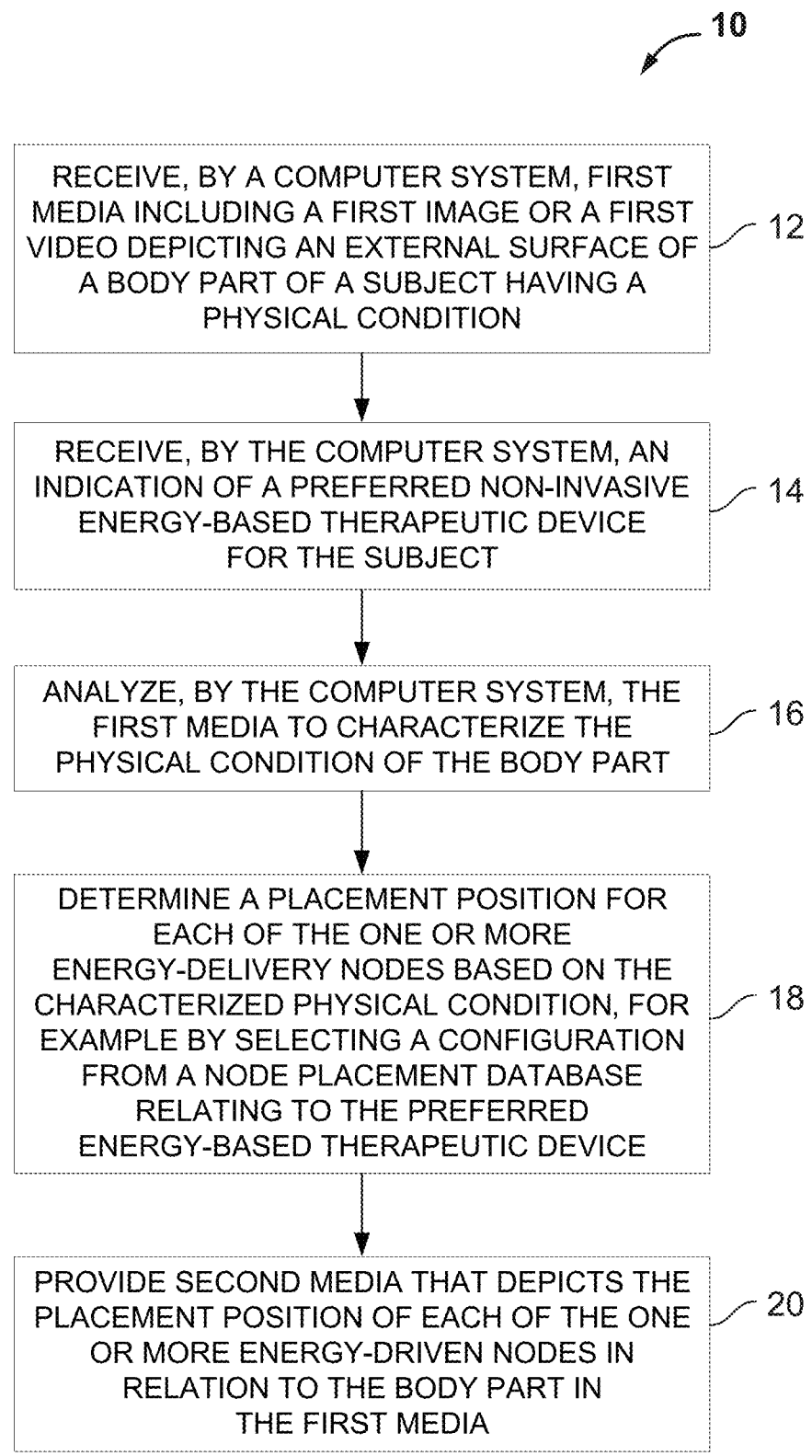
FIG. 1A is a flowchart illustrating a method for providing guidance on use of an energy-based therapeutic device to treat a physical condition according to one embodiment.

FIG. 1A is a flowchart illustrating a method 10 for providing guidance on use of an energy-based therapeutic device to treat a physical condition according to one embodiment. The method 10 can identify one or more placement locations for one or more energy-delivery nodes of an energy-based therapeutic device (such as any of the devices discussed herein). The method 10 begins at step 12, when a computer system receives a first media including a first image or a first video depicting an external surface of a body part of a subject having a physical condition. The computer system can be one or more of any number of suitable computing devices (such as but not limited to one or more servers, personal computers, tablets, smartphones, and the like). The computer system includes a communications port and computer processing circuitry, such as a processor, in communication with at least one non-transitory computer readable medium storing a node placement database configured to store a plurality of node placement configurations and optionally a pathology database. A pre-established media library may include the stored node placement configurations and the optional pathology database in one example. As described in greater detail below with reference to step 18, the processor can include a placement-position processor configured to process the image or video using the pre-established media library to determine a placement position for each of one or more energy-delivery nodes of an energy-based therapeutic device.

At step 14, the computer system receives an indication of a preferred non-invasive energy-based therapeutic device for the subject. The energy-based therapeutic device can be configured to administer a therapy using one or more energy-delivery nodes. Non-limiting examples of an indication that can be provided at step 14 include: an identification of a particular energy-based device; a preference for one or more vendors of non-invasive energy-based devices; cost-based preferences; or another similar indication provided by a system user (e.g., a patient, clinician).

Moving next to step 16, the computer system analyzes the first media to characterize the physical condition of the body part. At step 18, a placement position is determined for each of the one or more energy-delivery nodes based on the characterized physical condition. In one example, a placement position is determined by selecting one or more configurations from the node placement database relating to the preferred energy-based therapeutic device. In another example, the placement position is determined for each of the one or more energy-delivery nodes based on the characterized physical condition, where the placement position is selected from a plurality of node placement configurations corresponding to the preferred energy-based therapeutic device.

The following non-limiting examples are provided to further illustrate embodiments of step 18 of the method 10. In one example, the computer system receives at step 14 an indication of a preferred energy-based therapeutic device ("DEVICE A") which includes three energy-delivery nodes. A physical condition is characterized at step 16 as muscle fatigue. The node placement database may include a plurality of node placement configurations, five of which relate to preferred "DEVICE A." Suitable node placement configurations relating to "DEVICE A" may be selected from the node placement database based on different factors. For example, a node placement configuration may be deemed to relate to an energy-based therapeutic device based on, for example, the number of energy-delivery nodes included in the device, the maximum energy deliverable by the device, the number of times a device is intended to be used, or another factor. In this example embodiment, a placement position can be determined at step 18 for each of the three energy-delivery nodes of "DEVICE A" based on the characterized physical condition of muscle fatigue, where the placement position determined for each node corresponds to one of the five node placement configurations relating to "DEVICE A." In another example, a physical condition may be characterized at step 16 as edema. In this instance, a placement position can be determined at step 18 in which the placement position of each of the three energy-delivery nodes of "DEVICE A" corresponds to a different of the five node placement configurations relating to "DEVICE A." Had the computer system received at step 14 an indication of a different preferred energy-based therapeutic device ("DEVICE B" having two energy-delivery nodes, for example), a different subset of the plurality of node placement configurations in the node placement database may be deemed to relate to "DEVICE B," and the system may determine a different placement position at step 18 based on the determined physical condition and the indication of preferred "DEVICE B." These examples are intended to illustrate various implementations of step 18, and are not intended to limit the scope of the present disclosure.

At step 20, a second media is provided that includes the determined placement position for each of the one or more energy-delivery nodes, the second media including a second image or a second video that depicts the placement position of each of the one or more energy-delivery nodes in relation to the body part depicted in the first media.

Following step 20, the user may implement the information provided by the second media to place the one or more energy delivery nodes in the appropriate position for the physical condition indicated in the first media received in step 12. Once the energy-delivery nodes are in place, the user may activate the energy-based therapeutic device to deliver the appropriate energy-based therapy and address the physical condition.

Various implementations of the methods and systems for providing guidance on the use of a non-invasive energy-based therapeutic device are now described. For ease of illustration, and not by way of limitation, the implementations may be described by reference to the electrodes on an electrotherapy therapy device. However, the systems and methods are applicable to other energy-based therapeutic devices, regardless of whether the devices apply energy to a body part using electrodes.

Figure 1B:
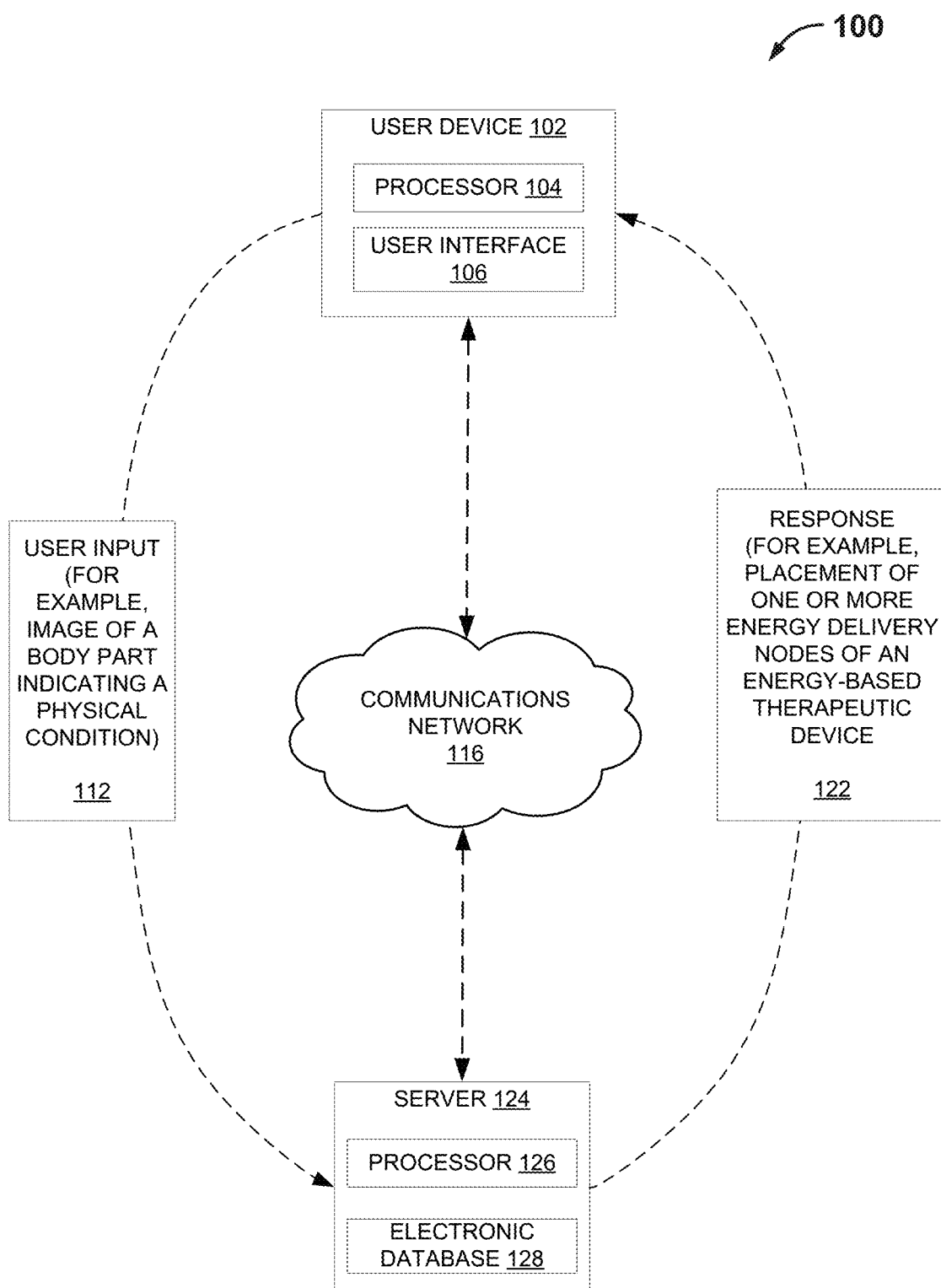
FIG. 1B is a block diagram of a computerized system for providing guidance on use of an energy-based therapeutic device according to one embodiment.
Figure 1C:
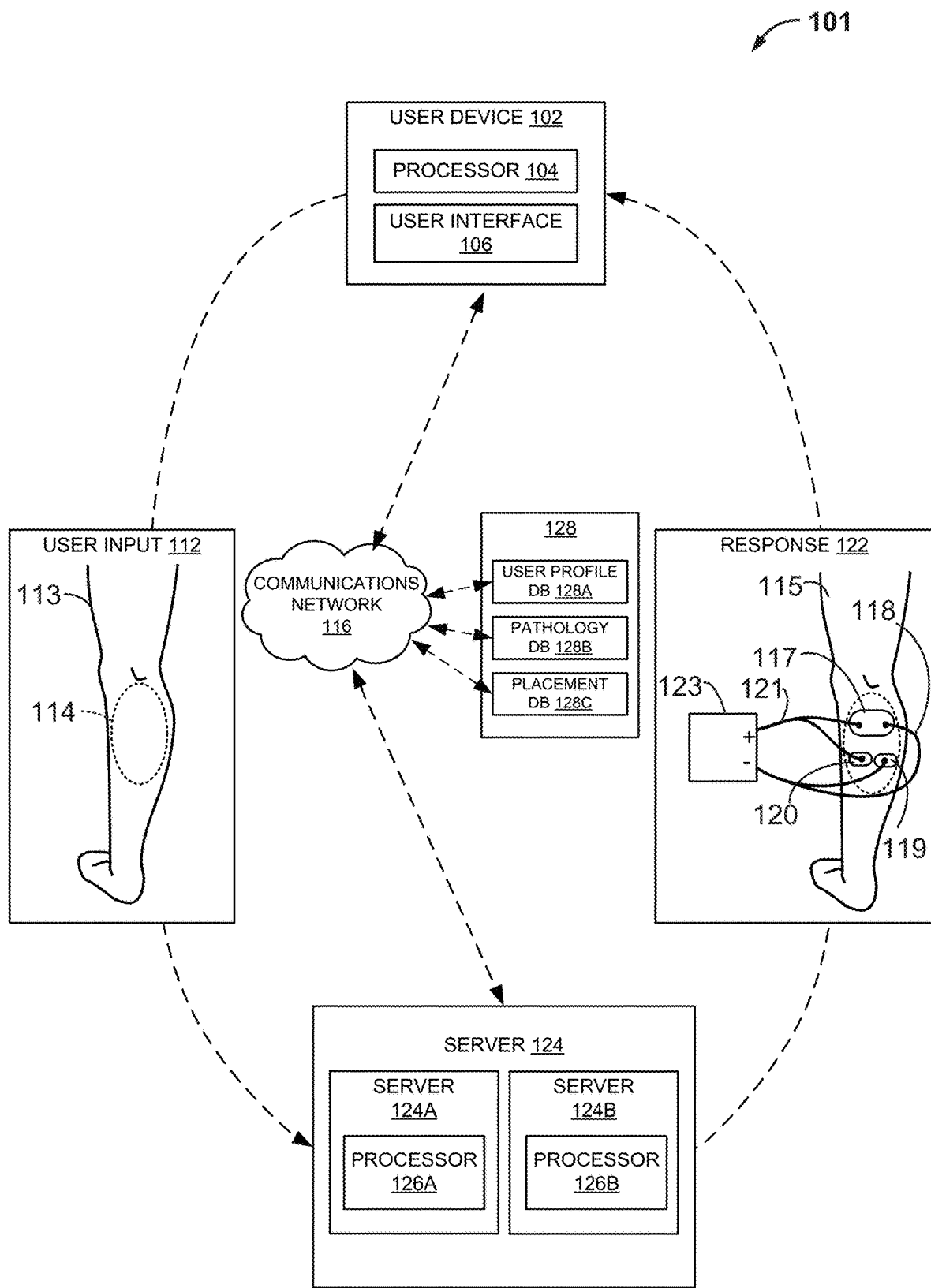
FIG. 1C is a block diagram of a computerized system for providing guidance on use of an energy-based therapeutic device according to another embodiment.
Figure 1D:
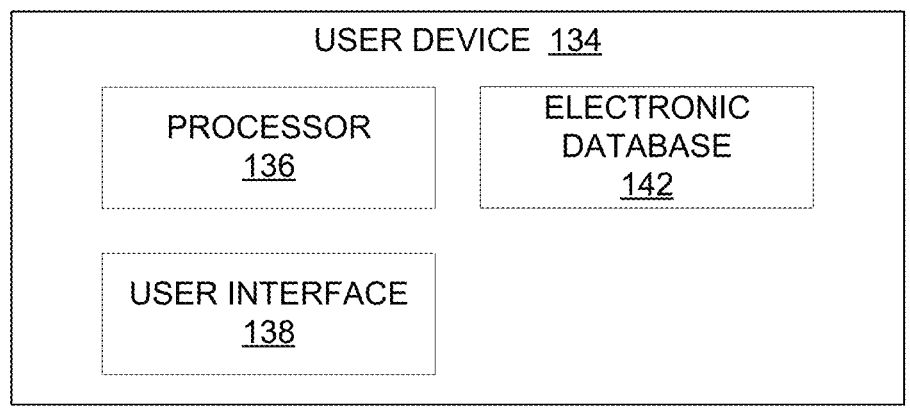
FIG. 1D is a functional block diagram illustrating a user device according to one embodiment.

FIGS. 1B, 1C, and 1D depict example embodiments of network and database structures that may be used to implement the systems and methods described herein. FIG. 1B is a block diagram of a computerized system 100 for providing guidance on use of an energy-based therapeutic device according to one embodiment of the present disclosure. Generally, in system 100, a user device 102 and a server 124 are connected over a communications network 116. The user device 102 can include a processing circuitry, such as a processor 104, and a user interface 106. The server 124 can include a processing circuitry, such as a processor 126, and an electronic database (DB) 128. In one implementation, a user sends a user input 112 to the server 124 to request guidance for treatment. In this non-limiting example, the user input 112 includes an image or a video of a user's body part indicating the location of a physical condition in need of treatment. The processor 126 analyzes the user input 112 and provides guidance on the treatment of the physical condition. For example, the processor 126 may characterize the physical condition in the user input 112 and/or further determine a suitable electrotherapy device, using electronic database 128, to treat the identified physical condition. In one embodiment, the processor 126 is a placement-position processor configured to process the user input to determine a placement position for each of one or more energy-delivery nodes of an energy-based therapeutic device. The electronic database 128 may include a pre-established media library, and the placement-position processor 126 may analyze the user input 112 using the pre-established media library in one example.

The server 124 may then respond to the user input 112 by sending a response 122 to the user device 102. The response 122 may include recommended placement positions of one or more electrodes of the selected electrotherapy device superimposed on the image or video sent by the user in the user input 112. In some implementations, the response 122 includes a list of recommended electrotherapy devices suitable to treat the physical condition.

Various implementations of the system 100 are now described. As used herein, "user device" includes, without limitation, any suitable combination of one or more devices configured with hardware, firmware, and software to carry out one or more of the computerized techniques described herein. User device 102 can be any computing device that is capable of receiving user input and of providing guidance to a user either as a stand-alone device or in communication with an external processing system over a communication network. For example, user device 102 can include a mobile computing device (e.g., a laptop computer, a tablet computer, a personal digital assistant (PDA), a mobile telephone (such as a smartphone), a camera, or the like). In other embodiments, the user device 102 includes a stationary computing device (e.g., a personal computer, stationary telephone, or other computing device). In some implementations, the user device is integrated with a medical device (such as an electrotherapy device to be used for providing the desired treatment). The user device 102 may be capable of wireless communications for interfacing with external systems. However, devices without wireless communications capabilities may be used without departing from the scope of the disclosure. The user device 102 may include a front-facing camera or a rear-facing camera for capturing images or video of specific parts of the body. In some implementations, the user device 102 is a device worn by a user such as augmented reality glasses. The user device 102 may also include software for generating or editing images or video, including software for generating a visual representation of a body part based on information provided by the user input 112.

As used herein, the term "processor," "processing circuitry," or "computing device" refers to one or more computers, microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. It may also refer to other devices configured with hardware, firmware, and software to carry out one or more of the computerized techniques described herein. Processors and processing devices may also include one or more memory devices for storing inputs, outputs, and data that are currently being processed. An illustrative computing device 200, which may be used to implement any of the processors and servers described herein, is described in detail below with reference to FIG. 2. In one embodiment, the server 123 of the system 10 includes a placement-position processor 126 configured to process the user input 112 to determine a placement position for each of one or more energy-delivery nodes of an energy-based therapeutic device.

As used herein, "user interface" includes, without limitation, any suitable combination of one or more input devices (e.g., keypads, touch screens, trackballs, voice recognition systems, gesture recognition systems, accelerometers, RFID and wireless sensors, optical sensors, solid-state compasses, gyroscopes, etc.) and/or one or more output devices (e.g., visual displays, speakers, tactile displays, printing devices, etc.). For example, user interface 106 described with reference to FIG. 1B can include a display (which may be a touch-sensitive color display, optical projection system, or other display) for graphically receiving and providing information to the user. Other examples of user interface 106 include a remote controlled interface, a mouse, trackball, keypad, keyboard, stylus input, joystick, voice recognition interface, and the like.

In some embodiments, the server 124 and the user device 102 are coupled to each other over a communications network 116. The communications network 116 may be any suitable network for exchanging information between the user device 102 and the server 124. For example, the communications network 116 can include the Internet, a mobile phone network, mobile voice or data network (e.g., a 4G or LTE network), cable network, public switched telephone network, a satellite network, or other type of communications network or combinations of communications networks. The user device 102 and the server 124 can communicate using one or more communications paths, such as, a satellite path, a fiber-optic path, a cable path, a path that supports Internet communications, free-space connections (e.g., for broadcast or other wireless signals), or any other suitable wired or wireless communications path or combination of such paths.

In the interest of simplicity, only one server and one user device are shown in FIG. 1B, however the skilled artisan will appreciate that the system 100 can support multiple servers and multiple user devices, as described in additional detail below with reference to FIG. 1C and throughout this disclosure. Multiple servers may operate together as a cluster or as a distributed computing network. The components of the system 100 of FIG. 1B may be arranged, distributed, and combined in any number of ways. For example, FIG. 1C is a block diagram illustrating another embodiment of the present disclosure in which a computerized system 101 distributes the components of system 100 over multiple processing and storage devices connected via the network 116. Such an implementation may be appropriate for distributed computing over multiple communication systems including wireless and wired communication systems that share access to a common network resource.

Returning again to FIG. 1B, the system 100 is implemented in some embodiments in a cloud computing environment in which one or more of the system components are provided by different processing and storage services connected via the Internet or other communications system. In a cloud computing environment, various types of computing services for content sharing, storage or distribution (e.g., video sharing sites or social networking sites) are provided by a collection of network-accessible computing and storage resources. For example, the cloud can include a collection of server computing devices, which may be located centrally or at distributed locations that provide cloud-based services to various types of users and devices connected via a network such as the Internet via communications network 116. These cloud resources may include one or more content sources and one or more data sources. In addition or in the alternative, the remote computing sites may include other user devices, such as a user medical device, a user computer device, and/or a wireless user communications device. For example, the other user devices may provide access to a stored copy of a video or a streamed video. The user devices may operate in a peer-to-peer manner without communicating with a server 124. The cloud can provide access to services, such as content storage, content sharing, or social networking services, among other examples, as well as access to any content described below, for user devices.

Services can be provided in the cloud through cloud computing service providers, or through other providers of online services. For example, the cloud-based services can include a content storage service, a content sharing site, a social networking site, or other services through which user-sourced content is distributed for viewing by others on connected devices. These cloud-based services may allow a user device to store content to the cloud and to receive content from the cloud rather than storing content locally and accessing locally-stored content. Cloud resources may be accessed by a user device 102 using, for example, a web browser, a desktop application, a mobile application, and/or any combination of access applications. In some implementations, a user device receives content from multiple cloud resources simultaneously. For example, a user device can stream video from one cloud resource while downloading/uploading content from a second cloud resource. Or, in another example, a user device can download/upload content from multiple cloud resources for more efficient downloading/uploading.

Similar to the system 100 of FIG. 1B, the computerized system 101 in FIG. 1C includes a user device 102, an electronic database 128, and a server 124. The user device 102 includes processing circuitry, such as a processor 104, and a user interface 106. As discussed above, the user device 102 may be any suitable device, including an electrotherapy device owned or used by the user. In this embodiment, the server 124 is a distributed system of servers that includes server instances 124A and 124B, each including processors 126A and 126B respectively. The server instances 124A and 124B may be, for example, virtual servers that are instantiated in a cloud computing environment. For simplicity, FIG. 1C depicts just two instances of the server 124. However, any suitable number of servers may be used. Similarly, although FIG. 1C shows only one user device 102, system 101 can support multiple user devices simultaneously.

The electronic database 128 may include separate databases, overlapping databases, or a distributed system of databases. The electronic database 128 can include a user profile database 128A, a pathology database 128B, and a placement database 128C. In one embodiment, the electronic database 128 includes a pre-established media library. In one example described in greater detail below with reference to the placement database 128C, the pre-established media library can store a plurality of node placement configurations. It will be understood that the electronic database 128 included in the server 124 of FIG. 1B can also include a user profile database 128A, a pathology database 128B, and a placement database 128C. The electronic database 128 may include additional resources that are helpful to the server 124 to determine placement positions of one or more electrodes of a suitable electrotherapy device to treat a physical condition.

For example, the user profile database 128A can store information related to a user. The user profile database 128A may include each user's personal information such as age, sex, height, weight, other demographic information, emergency contact information, etc. The user profile database 128A may also include user's medical information such as current physical condition, past medical history, pathology images, primary care physician, prior guidance provided, and other medical records. Besides personal and medical information, the user profile database 128A may also include other relevant information such as user-owned devices used to access the system 101, purchasing history of the user, details regarding special medical condition, images of various body parts of the user with or without physical injuries, user preferences (e.g., cost constraints on products, and user preferences on vendors). In another non-limiting example, the user profile database 128A can include information pertaining to various user activities such as athletic, physical, and/or outdoor activities that may make him/her prone to specific types of physical injuries. The user database 128A may serve to provide more personalized care for individual medical requirements or physical matters.

The pathology database 128B may include information useful for characterizing a variety of physical conditions. In one embodiment, the pathology database 128B includes a multimedia repository of links, images, text, and web pages related to searchable collections of histology and histopathology information, information on human anatomy, information on human physiology, X-ray images, MRI (Magnetic Resonance Imaging) images, CT (X-ray Computed Tomography) scan images, information on the skeletal system, information on the muscular system, anatomy of physical injuries, anatomy of sports injuries, and/or data and images on functional anatomy for movement and injuries. The pathology database 128B may be coupled via the network 116 to professional medical databases and other medical data resources. In some embodiments, a processor in the computerized system 101 (such as, for example, processor 104, 126A, or 126B) may perform a search of on-line resources or databases for pathology information. In one non-limiting example, the pathology database 128B is configured to cause one of the processors in the computerized system 101 to perform a targeted search of online resources for specific medical information using any number of known web-search algorithms for information related to a particular user or to a particular disease or physical condition.

The placement database 128C can include includes a plurality of node placement configurations. In one example, the placement database 128C can include a pre-established media library storing a plurality of node placement configurations. A subset of the node placement configurations stored in the placement database 128C may include node placement configurations that relate to a particular energy-based therapeutic device, such a preferred energy-based therapeutic device. The placement database 128C can include information on a variety of medical devices, including in particular information on electrotherapy devices. For example, the placement database 128C may include information on device settings such as current, frequency, polarity, amplitude, modulation, waveform, duration of therapy, etc. The placement database 128C may also include information on device usage such as detailed operation manuals, placement guides, treatment plans for various physical conditions, pad or other node sizes, details on safety and ease of operation, energy transfer mechanisms, vendor support, customer reviews, and the like. The database 128C can include detailed information related to laser light devices, prosthetic devices, minimally invasive surgical electrodes, defibrillators, non-invasive resuscitation devices, noninvasive hemodynamic monitoring devices, transcutaneous electrical nerve stimulators, drug delivery devices, iontophoresis electrodes, interferential current devices, multiple waveform electrotherapy devices, rehabilitation devices, shortwave diathermy devices, electronic muscle stimulators, neuromuscular stimulation (NMES) devices, pelvic floor stimulation devices, home traction devices, pneumatic traction devices, devices for treatment for dysphagia, swelling reduction devices, pulse taking devices, devices for gauging blood pressure, electrocardiography (EKG) devices, patient-monitoring systems for conditions including diabetes and/or cardiovascular diseases, etc. The foregoing list is not intended to be an exhaustive list of available options, and the placement database 128C can include other information on one or more medical devices and node placement configurations relating to those devices. The databases described above can be dynamic databases in which new information is continuously added and existing information updated and utilized to make decisions.

In the implementation illustrated with reference to FIG. 1C, the database components are connected to the server 124 and the user device 102 over a communications network 116. The arrangement and numbers of components shown in FIGS. 1B and 1C are intended to be illustrative, however, and any suitable configuration may be used.

As described with reference to FIG. 1B, a user implementing the computerized system 101 of FIG. 1C may send a user input 112 to the server 124 to request guidance on use of an electrotherapy device to treat a physical condition. The user input 112 may include a first media 113 corresponding to a body part. In this example, the body part depicted or indicated in the first media is the user's right leg. However, the media may be associated with any body part of the user. The first media 113 can be an actual, live, and/or real-time image or video of a body part streamed over network. The first media 113 may be a two-dimensional or a three-dimensional image or video.

In another non-limiting example, the first media 113 can include an image generated (e.g., computer generated image) by the user device 102 based on information provided by the user. For example, the user device can be equipped with an image generation software application that receives input from the user regarding the location of an injury, body measurement information, and other demographic information (e.g., age, gender, etc.) and generates an image in the likeness of the indicated body part without relying on an actual photograph of the body part.

A user can use the user interface to indicate the location 114 (indicated by dashed lines in FIG. 1C) and other characteristics (e.g., the size and shape) of a physical injury on the first media 113. For example, a user can use a keyboard associated with the user interface 106 to provide additional information about the physical condition such as how the injury was sustained, the severity of any pain experienced, etc. The user may also provide other user-related information with the user input 112, such as but not limited to treatment preferences and health history. The user device 102 is adapted or configured with a graphical user interface (GUI), which may be web-based or otherwise, for providing the user input 112 and receiving medical guidance. Additional embodiments of the user input 112 are discussed in detail below with reference to FIG. 5.

One or more processors in the server 124, such as processor 126A and/or processor 126B, can analyze the user input 112 using data from the electronic database 128. For example, one or more of the processors 126A, 126B may update the user profile database 128A based on data received from the user input 112. Using the user profile database 128A and the pathology database 128B, the processing circuitry included in server 124 can characterize the physical condition described or indicated in the user input 112. The physical condition may be present in the location 114 identified by the user in the user input 112 or it may be present in a location other than 114. The physical condition may be any medical condition treatable using an electrotherapy device, including, without limitation, any one or a combination of musculoskeletal disorder, neurological disorder, orthopedic disorder, soft-tissue disorder, tissue damage, pain, muscle spasms, post-surgical conditions, swelling, urine or fecal incontinence, muscle fatigue and/or any physical condition that can be treated by an electrotherapy device. The electrotherapy device can be any medical device present in the placement database 128C. The physical condition may include a medical condition (acute, such as immediate pain, tenderness, swelling, etc. and/or chronic, such as diabetes, arthritis, asthma, etc.) and/or symptoms accompanying a medical condition such as pain, bruising, swelling, etc. Example algorithms that can be used by the processor 126 (FIG. 1B) and the processors 126A, 126B (FIG. 1C) to analyze the user input 112, characterize the physical condition, and determine appropriate devices to treat a physical condition are discussed in greater detail with reference to FIGS. 4A and 4B below.

The processing circuitry included in the server 124 (such as the processor 126 of FIG. 1B or the processors 126A, 126B of FIG. 1C) can provide guidance to the user to treat the physical condition indicated in the user input 112. In the implementations illustrated in FIGS. 1B and 1C, the guidance includes a guidance response 122 transmitted to the user, via the user device 102, from the server 124. Although the methods and systems described herein are suitable for providing guidance to any user of an electrotherapy device including patients and clinicians, node placement and other guidance provided by the computerized system 101, such as that included in guidance response 122, can be designed so that a patient without professional medical training can follow the guidance to correctly apply the treatment. In one embodiment, the processing circuitry included in the server 124 (124 (such as the processor 126 of FIG. 1B or the processors 126A, 126B of FIG. 1C) is a placement-position processor configured to process a plurality of images or videos using the electronic database 128 to determine a placement position for each of one or more energy-delivery nodes of an energy-based therapeutic device.

In some implementations, the guidance is prepared specifically for use by a patient based on a recommendation or a prescription from a clinician treating the patient. Medical guidance can include placement information for the particular electrotherapy device, determined based on characteristics of the specific condition and information associated with the user. The recommendation may be based on an electrotherapy device specified by the user (e.g., a device already owned or preferred by the user). In some embodiments, processing circuitry included in the server 124 (such as the processor 126 of FIG. 1B or the processors 126A, 126B of FIG. 1C) may also recommend a suitable electrotherapy device for effective treatment. For example, the electrotherapy device may be recommended based on a specific vendor or a specific user preference such as cost. The response may also include recommended sizes and a number of electrodes to use.

Processing circuitry in the server 124 can determine and recommend placement positions 117, 119, and 120 of one or more electrodes 118 and 121 of an electrotherapy device 123. The electrotherapy device 123, which is depicted in second media 122, can be incorporated into the computerized system 101. The user device 102 may include the electrotherapy device 123 in one example. In one embodiment, the electrotherapy device 123 is a standalone system independent of the user device 102 and external to the computerized system 101.

The processing circuitry (such as the processor 126 of FIG. 1B or the processors 126A, 126B of FIG. 1C) can then indicate the recommended placement positions as part of the guidance response 122. The guidance response 122 may further provide instructions for the user device 102 to annotate the placement positions 117, 119, and 120 on the first media 113. In such an embodiment, the processing circuitry included in the server 124 may use the first media 113 to graphically indicate the recommendations provided by the guidance response 122. The electrotherapy device 123 may be selected from the placement database 128C and can be a medical device that is capable of treating the physical condition.

In some implementations, instead of annotating the first media 113, the guidance response 122 received by the user device 102 includes a second media 115 overlaid with placement positions 117, 119, and 120 of one or more electrodes 118 and 121 of the electrotherapy device 123. The second media 115 may be an actual image of the user's body part annotated with the placement positions 117, 119, and 120, as shown in the example embodiment of FIG. 1C. The user input 112 and the received guidance response 122 may be combined as a single display or may be implemented as separate displays. The user input 112 and the received guidance response 122 may be indicated as separate options within the same GUI. The user input 112 and the received guidance response 122 can also be on separate user devices with separate user interfaces. Several example implementations of the guidance response 122 are discussed below with reference to FIG. 6 and step 310 of FIG. 3.

Although FIGS. 1B and 1C depict network-based systems for providing guidance on use of an electrotherapy device to treat a physical condition, the functional components of the system 100 and the system 101 may be implemented as one or more components included with or local to the user device 102. For example, FIG. 1D depicts a user device 134 according to another embodiment that includes processing circuitry, such as a processor 136, a user interface 138, and an electronic database 142. The processor 136 may be configured to perform any or all of the functions of the processor 104 of FIGS. 1B and 1C, the processor 126 of FIG. 1B, and the processors 126A, 126B of FIG. 1C. The electronic database 142 may be configured to store any or all of the data stored in databases 128 of FIGS. 1B and 1C, and the user interface 138 may be configured to perform any of the input and output functions described herein for the user interfaces 106 of FIGS. 1B and 1C. Additionally, the functions performed by each of the components in the systems of FIGS. 1B, 1C, and 1D may be rearranged. In some implementations, the processor 136 (FIG. 1D) performs some or all of the functions of the processor 126 (FIG. 1B) and/or the processors 126A, 126B (FIG. 1C) as described herein. For example, the processor 136 in one embodiment may compute, using the electronic database 142 included in the user device 134, the placement positions of one or more electrodes of an electrotherapy device. Another processor (such as processor 104 of user device 102) may then superimpose the electrode positions on the first media 113 to provide customized guidance on the use of the electrotherapy device 123 to the user. This customized guidance may be provided to the user through the user interface 138 of the user device 138. Although the remainder of this disclosure may describe providing customized guidance on the use of an electrotherapy device with reference to the system 100 of FIG. 1B, any of the systems of FIGS. 1B, 1C, and 1D may be used, as well as any suitable variations of these systems.

Figure 2:
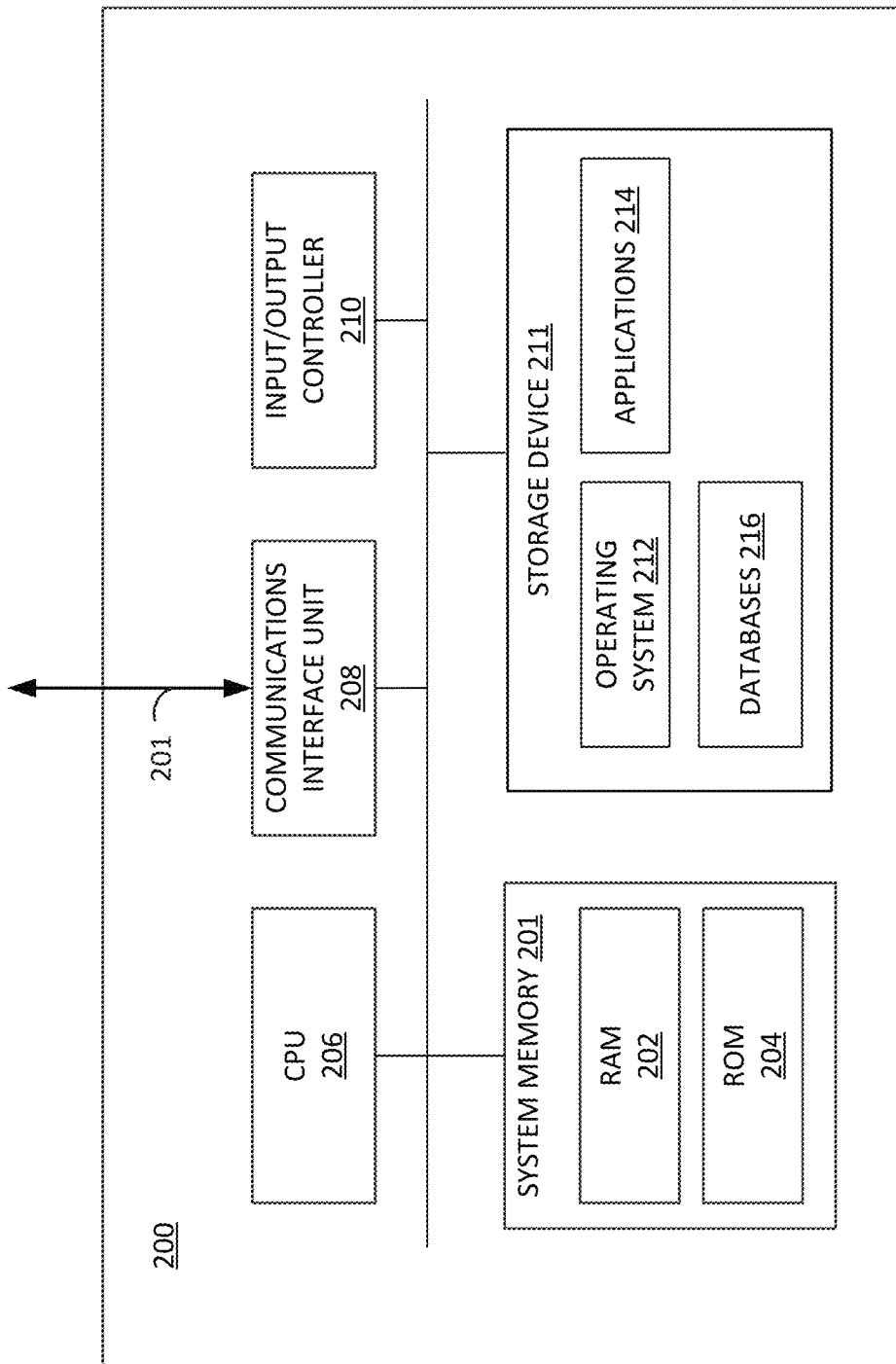
FIG. 2 is a block diagram illustrating components of a computing device according to one embodiment.

FIG. 2 is a block diagram illustrating components of a computing device 200 according to one embodiment of the present disclosure. Each of the components of the computerized systems 100 and 101 described with reference to FIGS. 1B, 1C, and 1D may be implemented on one or more computing devices 200. The components of the computing device 200 can be configured to perform any of the processes described herein, such as processes performed by components in the computerized systems 100 and 101 described with reference to FIGS. 1B, 1C, and 1D. In certain aspects, a plurality of the components of a computerized system described herein (such as computerized system 100 or 101) may be included within one computing device 200. In certain implementations, a component and a data storage device of a computerized system described herein may be implemented across several computing devices 200. The computing device 200 can include at least one communications interface unit 208, an input/output controller 210, system memory 201, and one or more data storage devices 211. The system memory 201 includes at least one random access memory (RAM) 202 and at least one read-only memory (ROM) 204. These elements are in communication with a central processing unit (CPU) 206 to facilitate the operation of the computing device 200.

The computing device 200 may be configured in many different ways. For example, the computing device 200 may be a conventional standalone computer or alternatively, the functions of computing device 200 may be distributed across multiple computer systems and architectures. In the implementation illustrated in FIG. 2, the computing device 200 is linked, via network or local network, to other servers, systems, or other computing devices 200. For example, a link between the communications interface unit 208 of the computing device 200 and other components external to the computing device 200 is shown schematically with arrow 201. The computing device 200 may be configured in a distributed architecture, wherein databases and processing circuitry (in the form of one or more processors for example) are housed in separate units or locations. Some units or locations can perform primary processing functions and contain at a minimum a general controller or a processor and a system memory. In distributed architecture implementations, each of these units may be linked or attached via the communications interface unit 208 to a communications hub or port (not shown) that serves as a primary communication link with other servers, client or user computers, and other related devices. The communications hub or port may have minimal processing capability itself, serving primarily as a communications router. A variety of communications protocols may be part of the system, including, but not limited to, Ethernet, SAP, SAS™, ATP, BLUETOOTH™, GSM, DICOM, and TCP/IP.

The communications interface unit 208 can be any suitable combination of hardware, firmware, or software for exchanging information with external devices. Communications interface unit 208 may exchange information with external systems using one or more of a cable modem, an integrated services digital network (ISDN) modem, a digital subscriber line (DSL) modem, a telephone modem, an Ethernet card, or a wireless modem for communications with other devices, or any other suitable communications interface. Such communications may involve the Internet, a communications network 116 described with reference to FIGS. 1B and 1C, or any other suitable communications network. In addition, the communications interface unit 208 may include circuitry that enables peer-to-peer communication, or communication between user devices in locations remote from each other.

The CPU 206 can include a processor, such as one or more conventional microprocessors and one or more supplementary co-processors such as math co-processors for off-loading workload from the CPU 206. The CPU 206 can be in communication with the communications interface unit 208 and the input/output controller 210, through which the CPU 206 communicates with other devices such as other servers, user terminals, or devices. The communications interface unit 208 and the input/output controller 210 may include multiple communication channels for simultaneous communication with, for example, other processors, servers, or client terminals.

The CPU 206 can also be in communication with the data storage device 211 and system memory 201. The data storage device 211 and system memory 201 may include an appropriate combination of magnetic, optical, or semiconductor memory, and may include, for example, RAM 202, ROM 204, a flash drive, optical media such as a compact disc, or a hard disk or drive. The system memory 201 may be any suitable combination of fixed and/or removable memory, and may include any suitable combination of volatile or non-volatile storage. The system memory 201 may be physically located inside a user device 102 or a server 124 or may be physically located external to or outside of the user device 102 (e.g., as part of cloud-based storage) and accessed by the user device 102 over the communications network 116. The CPU 206 and the data storage device 211 each may be, for example, located entirely within a single computer or other computing device; or connected to each other by a communication medium, such as a USB port, serial port cable, a coaxial cable, an Ethernet cable, a telephone line, a radio frequency transceiver or other similar wireless or wired medium; or a combination of the foregoing. For example, the CPU 206 may be connected to the data storage device 211 via the communications interface unit 208. The CPU 206 may be configured to perform one or more particular processing functions.

The data storage device 211 may store, for example, (i) an operating system 212 for the computing device 200; (ii) one or more applications 214 (e.g., computer program code or a computer program product) adapted to direct the CPU 206 in accordance with the systems and methods described herein, and particularly in accordance with the processes described in detail with regard to the CPU 206; and/or (iii) database(s) 216 adapted to store information that may be utilized by a computer program product, such as one or more applications 214.

The operating system 212 and applications 214 may be stored, for example, in a compressed, an uncompiled, and/or an encrypted format that may include computer program code. The instructions of applications 214 may be read into a main memory of processing circuitry of the computing device 200 (such as CPU 206) from a computer-readable medium other than the data storage device 211, such as from the ROM 204 or from the RAM 202. While execution of sequences of instructions in the applications 214 causes the CPU 206 to perform the process steps described herein, hard-wired circuitry may be used in place of, or in combination with, software instructions for implementation of the processes of systems and methods described in the present disclosure. Thus, the systems and methods described herein are not limited to any specific combination of hardware and software.

Suitable applications 214 (e.g., "computer program code" or "computer program product") may perform one or more functions in relation to providing image-based guidance as described herein. The computing device 200 also may include program elements such as an operating system 212, a database management system, and "device drivers" that allow the processing circuitry of the computing device 200 (such as CPU 206) to interface with computer peripheral devices (e.g., a video display, a keyboard, a computer mouse, etc.) via the input/output controller 210.

The term "computer-readable medium" as used herein refers to any non-transitory medium that provides or participates in providing instructions to the processing circuitry of the computing device 200, such as CPU 206 (or any other processing circuitry or processor of a device described herein), for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying out one or more sequences of one or more instructions to the CPU 206 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 200 (e.g., a server) can receive the data on the respective communications line and place the data on a system bus for the processor of the computing device 200. The system bus carries the data to main memory, from which the processor retrieves and executes the instructions. The instructions received by main memory may optionally be stored in memory either before or after execution by the processor. In addition, instructions may be received via a communication port as electrical, electromagnetic, or optical signals, which are exemplary forms of wireless communications or data streams that carry various types of information.

Figure 3:
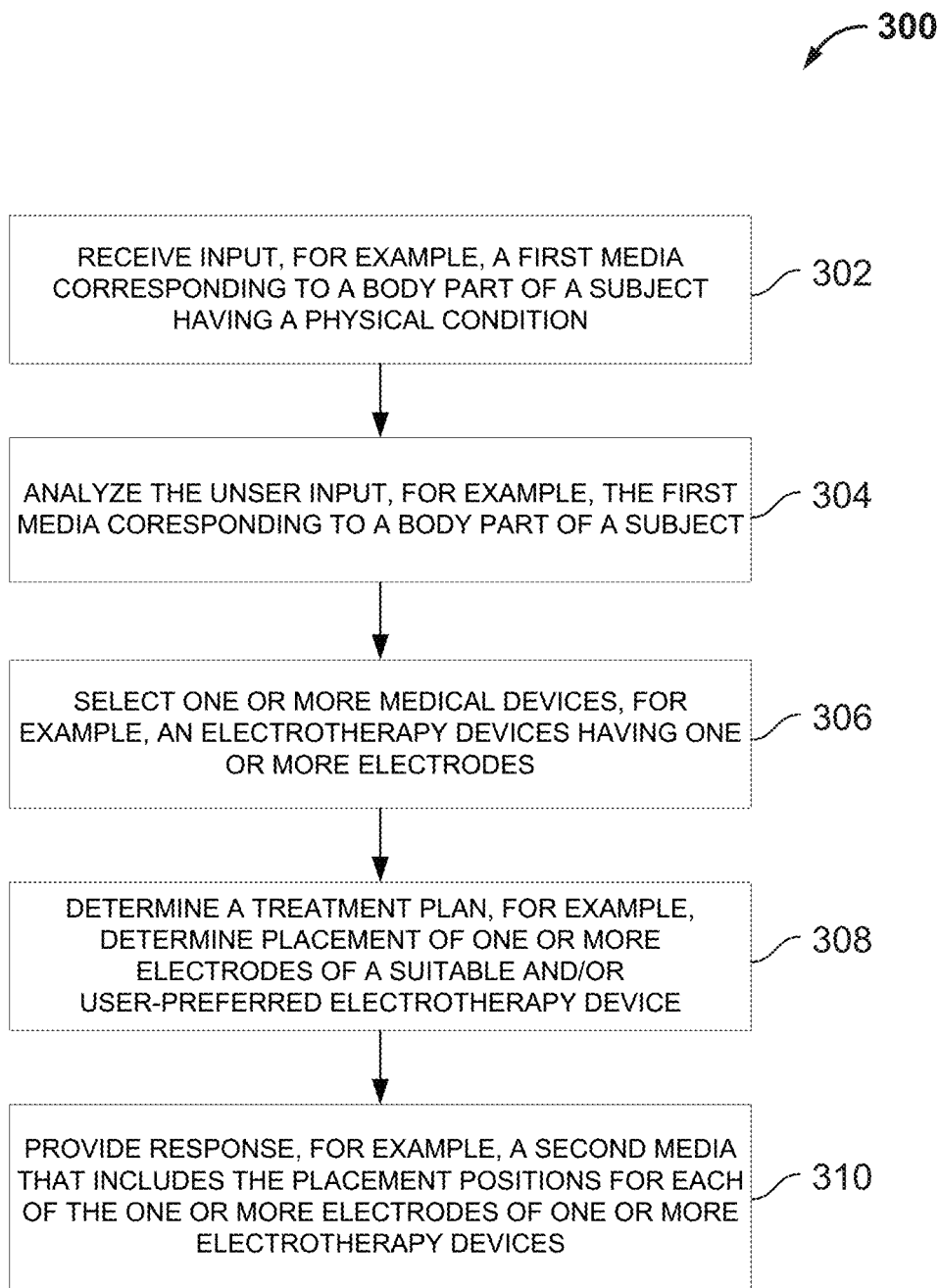
FIG. 3 is a flowchart illustrating a method for providing guidance on use of an energy-based therapeutic device to treat a physical condition according to another embodiment.

FIG. 3 is a flowchart illustrating a method 300 for providing guidance on use of an energy-based therapeutic device to treat a physical condition according to another embodiment of the present disclosure. The method 300 may be implemented by the system 100 in certain implementations, and is described with reference to a client-server implementation illustrated in FIG. 1B. However, the method 300 may be implemented using any of the system implementations described herein. In addition, the steps of the method 300 may be performed simultaneously, reversed, or some steps may be omitted.

Embodiments of the method 300 generally begin with step 302, in which a user device 102 sends a user input 112 to the server 124 to request guidance to treat a physical condition and the server 124 receives the user input 112. Prior to step 302, the process may include a step (not shown) in which a user authenticates with the server 124 (or indeed any processing circuitry in the system). In one example, the user authenticates by inputting a username and password (or providing other identification information) via user interface 106. The user may then be provided with an on-screen option (for example, by selecting a "My Profile Home" option as described with reference to FIGS. 5 and 6) to submit a request for guidance. In this embodiment of the method 300, step 302 includes the computerized system 100 receiving a first media corresponding to a body part of a subject having a physical condition in need of treatment. The input can be received via the user interface 106.

As will be described in greater detail below with reference to FIG. 5, a graphical user interface, such as user interface 106, can prompt or enable a user to provide information related to the physical condition for which treatment is sought. As explained in detail above, a user request or input can include media (e.g., the first media 113) corresponding to the medical condition for which guidance is sought. In this example, the user request includes media (e.g., video or an image) corresponding to a body part of a subject (which may be the actual user of the user device or a patient associated with the user of the user device) having the physical condition requiring treatment. The image or video can be an actual picture of the body part or a generated image to indicate the physical condition for which the user needs guidance.

The user may use any of the features of the user interface 106, discussed above with reference to FIG. 1, to indicate the location and other features of the physical condition on the first media 113. For example, the user can use a stylus or the tip of a finger on a touch-activated interface to encircle the area on the image where he is experiencing a physical condition such as pain or swelling. The user can describe the physical condition using keyboard or using voice to text recognition software on the user device. For example, the user can say "I'm experiencing pain in the upper part of my right leg." Using the display described in FIG. 5, the user may provide other additional information which may be useful for the server 124 in providing guidance to treat the physical condition. For example, the user may provide information on how the injury was sustained, the severity of any pain experienced, information on tenderness, any sores, previous medical condition, prior treatment applied, other abnormalities in the affected area, or other useful information.

Referring again to FIG. 3, the method 300 moves to step 304 in which the server 124 analyzes the user input 112 in response to the user request. In one embodiment, the server 124 analyzes the user input 112 based on data from the user profile database 128A and the pathology database 128B. Based on the analysis, the server 124 may determine, for example, that the user's right leg is swollen and is experiencing pain due to a particular underlying medical condition. The underlying medical condition may be determined by the server 124 based on information provided by the user, or may be provided to the system by the user based on a consultation with a clinician or a specialist. Example methods employed by the server 124 for analyzing the user input to characterize the physical condition and for determining a suitable electrotherapy device to treat the identified physical condition are described in detail with reference to FIGS. 4A and 4B.

Moving next to step 306, the server 124 determines an appropriate device to treat the identified physical condition. In one implementation, the server 124 selects one or more suitable electrotherapy devices, based in part on the user input 112 and/or information obtained from the placement database 128C, for treating the identified physical condition. The user input or the user's profile may include information regarding electrotherapy devices owned or preferred by the user. The user may also be provided the option to specify whether the system should limit the guidance to recommendations based on these owned or preferred devices. Based on the information available to the system and user-specified preferences, the server 124 selects a suitable electrotherapy device to treat the physical condition. In some cases where the user may have a preferred device, the appropriate device may be selected in addition to the user-preferred device. The appropriate device may be better suited to treat the physical condition than the user-preferred device.

The method 300 next moves to step 308, in which the server 124 generates guidance, such as guidance response 122, for treating the physical condition. The guidance may include one or more of, a recommended electrotherapy device, one or more of placement positions of one or more electrodes of the selected electrotherapy device, recommended sizes for the electrode pads, and where appropriate, stimulation levels and treatment duration required to achieve the desired therapeutic results.

At step 308, the server 124 can determine the placement positions of one or more electrodes of the electrotherapy devices selected in step 306. In one example, the server 124 determines a placement position for each of the one or more electrodes of the electrotherapy device selected at step 306 based on a characterized physical condition, the placement position selected from one of a plurality of electrode placement configurations stored in an electrode placement database. In another example, the placement position is determined for each of the one or more electrodes based on the characterized physical condition, where the placement position is selected from a plurality of electrode placement configurations corresponding to a preferred electrotherapy device. Thus, in some cases where the user may have a preferred device, the guidance response for treating the physical condition using the appropriate device may be determined in addition to determining a guidance response corresponding to the user-preferred device. The appropriate device may be better suited to treat the physical condition than the user-preferred device. For example, if the user indicated the "Empi Continuum"™ device from DJO Global Inc. as a preferred electrotherapy device, then the server 124 may determine the placement positions for both the electrodes of this device in addition to the placement positions of one or more electrodes of another appropriate (or potentially more suitable) device determined by the server itself. The server 124 may compare the efficacy of treatment using the user-preferred device and the appropriate device determined from its optimization algorithms.

The server 124 may simulate the therapy using a mathematical model to determine an optimum placement of one or more electrodes of the selected electrotherapy device. The server 124 may also apply various optimization techniques to optimize different parameters of the therapy. The data for optimization can be obtained from the user profile database 128A, pathology database 128B, and the placement database 128C. For example, the server 124 may optimize for the user's body structure, height weight, duration of the therapy, placement positions, or any other medical constraints associated with a particular user such as the presence of pacemakers or other medical implants in the user's body. The server 124 may further establish other requisite device settings customized to the user including current frequency, polarity, modulation, electrode pad sizes, waveform, and duration of therapy.

At step 310, the server 124 provides or transmits the guidance response 122 to the user. The response may be provided by e-mail, by posting an update to the user profile database 128, by text message, or by any suitable means for communicating recommendations to a user of the user device. In some implementations, the guidance response 122 includes a second media 115 overlaid with placement positions 117, 119, and 120. However, in some cases, the guidance response 122 may include software instructions for another device (for example, user device 102) to annotate the image or video provided in the user input request. This approach may be desirable where communications bandwidth is limited, so that the server need not communicate back to the user device a potentially large file including annotated images or videos. The processor 104 on the user device 102 can implement these directions to overlay graphical indications of the placement positions on the first media 113 already stored on the user device 102. In some implementations, the directions may be text-to-speech instructions guiding a user to place the electrodes on the placement positions.

The guidance response 122 may include additional information, such as but not limited to electrode pad sizes, etc., as discussed with reference to FIG. 6. The user device 102 may include a media projecting device and may project the placement positions 117, 119, and 120 directly on the real-life body part. The second media 115 can be the same as the first media 113 or it can be extrapolation of the first media in order to better indicate the placement positions 117, 119, and 120 for each of the one or more electrodes 118 and 121 of an electrotherapy device 123. The server 124 may also update the user profile database 128A by storing the user input 112 and/or the guidance response 122 to the corresponding user profile. An example display of the received response 122 is discussed in detail with reference to FIG. 6.

In some cases where the user may have a preferred device, the guidance response for treating the physical condition using the appropriate device may be provided in addition to a guidance response using the user-preferred device. As explained above, the appropriate device may be better suited to treat the physical condition than the user-preferred device. The response may include a comparison of the appropriate device determined by the server 124 and the user-preferred device. The response may include vendor-furnished incentives (for example, discounts) for the user to acquire the new device or new parts for the user-preferred device. In some implementations, guidance to the user may include advice regarding an appropriate course of action to treat the physical condition.

Figure 4A:
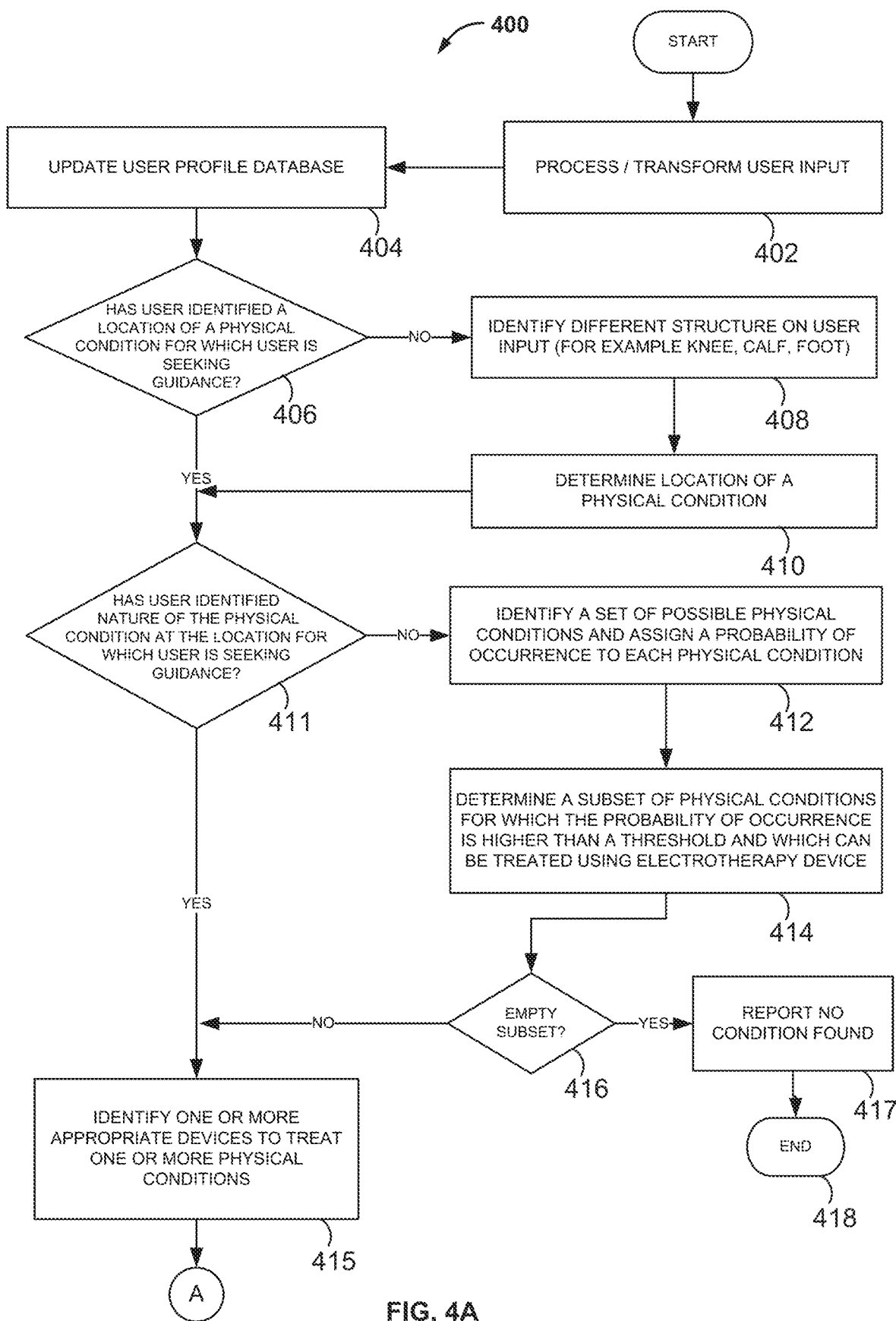
FIGS. 4A and 4B provide a flowchart illustrating a method for providing guidance on use of an energy-based therapeutic device to treat a physical condition according to yet another embodiment.
Figure 4B:
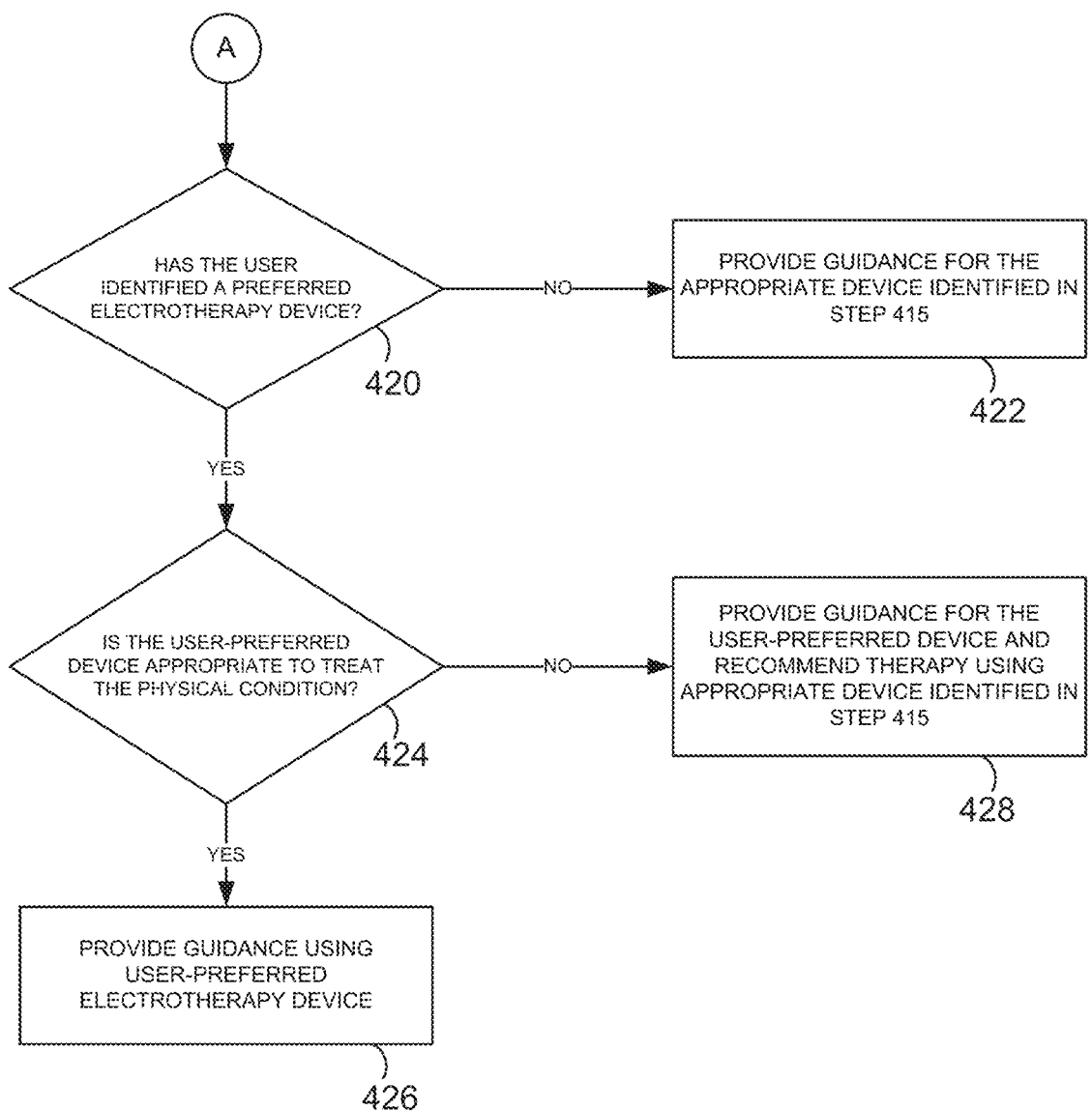

FIGS. 4A and 4B provide a flowchart illustrating a method 400 for analyzing the user input 112 to provide guidance (for example, a guidance response 122) to a user according to one embodiment of the present disclosure. In one example, the server 124 of FIG. 1B or FIG. 1C implements the method 400, but any processing circuitry in the systems described herein can implement embodiments of the method 400. Further, the steps of the method 400 may be performed simultaneously, reversed, or some steps may be omitted.

Specific steps of the method 400 will be described in the context of a client-server implementation illustrated in FIG. 1B, but the method 400 can be implemented using any of the system implementations described herein. Accordingly, the steps of the method 400 described below as being performed by any particular component of the system 100 may be performed by another component or a combination of components without departing from the scope of the present disclosure. Before the method begins at step 402, the server 124 can receive user input 112 requesting guidance to treat a physical condition. For example, implementations of the method 400 can be performed as part of the step 304 discussed above with reference to FIG. 3. Example implementations of user input 112 are discussed with reference to FIG. 5.

The method begins at step 402, in which the server 124 processes, transforms, and stores the received user input 112. The server 124 may process and transform the user input 112 into any suitable format. For example, portions of the user input 112 can be transformed and stored in a digital format such as DICOM (Digital Imaging and Communications in Medicine) format (".dcm"/".DCM" extension), which is an industry-wide standard for handling, storing, printing, and transmitting information in medical imaging. The server 124 may group information into data sets that contain a number of attributes (including items such as name, identification (ID), image pixel data, etc.) within the file so that the image is not separated from its attributes by mistake. Suitable data formats may also include attributes such as "frames," allowing storage of video loops or other multi-dimensional multi-frame data. These data formats may also encapsulate three- or four-dimensional data in a single object. Pixel data can also be compressed using a variety of standards, including JPEG, JPEG Lossless, JPEG 2000, and Run-length encoding (RLE).

In one embodiment, the user input 112 can be transformed to allow the server 124 to compare the user input 112, irrespective of the source, and further process it using commercially available image processing applications such as OsiriX, MATLAB, etc. The server 124 may further process the user input 112 to reduce any artifacts or noise in the image and harmonize media quality, such as by removing artifacts due to different exposure parameters, while simultaneously using information provided by the user including text or symptoms describing the physical condition.

Depending on the specific signal processing technique employed, the server 124 can use the information from the user input 112 and the user profile database 128A to construct a mathematical model including a multidimensional vector space. The server 124 may transform different sets of data into one coordinate system using linear or non-linear, elastic or non-rigid transformations, etc. The data obtained from the user input 112 can include one or more photographs, data from different sensors, from different times, or from different viewpoints. Thus, the vector space may include vectors that are categorical (including one of a set of unordered items, for example "male" or "female," etc.), ordinal (including one of a set of ordered items, for example "large," "medium," or "small"), integer-valued (for example a count of the number of occurrences of a particular word in the description of the physical condition) or real-valued (for example a user's body weight, height, etc.). In some implementations, the server 124 derives real-world coordinates from the user input 112 using information from the user profile database 128A and various mathematical methods including projective (epipolar) geometry, geometric algebra, rotation representation with exponential map, kalman and particle filters, nonlinear optimization, and/or robust statistics.

Moving next to step 404, the server 124 obtains the user profile for the subject from the user profile database 128A and updates the user profile database 128A based on new information in the user input 112. For example, the server 124 may update the user profile to reflect the user input 112 as the most recent request. User profile database 128A, as discussed in relation to FIG. 1C, contains information about the user such as height, weight, gender, past medical records, and the like. In one non-limiting example, if the user input 112 includes a picture of the user's leg which was not already present in the user profile database 128A, then the server 124 saves that picture and all the relevant information associated with that picture in the user profile database 128A for later use. The server 124 may also update the user profile to reflect changes in the subject's health or physical dimensions, such as weight. In this way, the databases described herein are dynamic and are updated regularly in light of new developments.

The method 400 continues to step 406, in which the server 124 analyze the user input and determines if the user has indicated a location of a physical condition for which the user is seeking treatment guidance. In one example, the location of a physical condition corresponds to the location 114 described with reference to FIG. 1C. If the user has identified the location, then the method 400 proceeds directly to step 411. Otherwise, the method 400 proceeds to step 408 to first identify the location of a physical condition in the user input 112. At step 408, the server 124 identifies different anatomical structures of a corresponding body part in the user input 112. For example, if the user input 112 is an image of the user's leg, then the server 124 identifies locations such as but not limited to the knee, ankle, and foot of the user's leg. In order to identify anatomical structures, the server 124 may use various algorithmic techniques to compare the user input 112 to images from the pathology database 128B. For example, the processor 126 may use various algorithms such as image processing, computer-vision, artificial intelligence, augmented reality, standard ABCDE (asymmetry, border, color, diameter, and evolution over time) algorithm, or computer-aided diagnosis to compare the image sent by the user to any past images of the user found in the user profile database 128A. The server 124 may further use various feature detection methods such as corner detection, blob detection, edge detection or thresholding, and/or other image processing methods to isolate differences and/or similarities between the user input 112 and images in the pathology database 128B. If part of the user input 112 is unknown, then techniques such as simultaneous localization and mapping (SLAM), for example, can be employed to map relative positions. If no information about the body part's geometry is available, then structure from motion methods like bundle adjustment can be used.

Moving next to step 410, the server 124 evaluates different anatomical structures identified in step 408 to identify one or many locations of one or more physical conditions. For example, the server 124 may evaluate the user's calf muscle, knee, ankle, and foot, as identified in step 408, to determine signs of abnormalities such as swelling, discoloration, and the like. In some implementations, the location of a physical condition is analogous to the various manifestations of a physical condition such as swelling, redness, etc. The server 124 analyzes individual anatomical structures for special characteristics such as compactness, form, size, location, reference to close-by structures, average grey level values, and proportion of grey level values within each feature using various pattern recognition algorithms. The server 124 extracts various features and compares them to the pathology database 128B to identify potential locations of one or many physical conditions. The server 124 can simultaneously identify more than one location, for example swelling in the calf muscle and redness in the foot. The information accessed from the pathology database 128B can be narrowed or expanded based on the user profile and the user input 112. If the user has identified the location (such as location 114 of FIG. 1C) of a physical condition then the server 124 proceeds directly to the step 411.

At step 411, the server 124 analyzes the user input and determines if the user has identified the nature of a physical condition at the location previously identified (by the user at step 406 or by the server 124 at step 410). If the user has identified the nature of the physical condition such as pain, edema, etc. at the identified location, then the method moves to step 415. Otherwise, the method moves to step 412, in which the server 124 identifies the physical condition for which the treatment guidance will be provided. In one non-limiting example, the user identifies the nature of the physical condition through the user input 112. For example, the user input 112 may specify the physical condition based, for example, on a consultation between the subject and a clinician or a specialist. In such cases, the server 124 obtains, from the pathology database 128B, information about the previously diagnosed condition so that appropriate treatment recommendations may be provided and the method 400 may proceed directly to step 415 to determine an appropriate medical device to treat the physical condition.

In cases where the user does not identify the nature of the physical condition and the method instead moves to step 412, the server 124 determines one or more possible physical conditions associated with the location identified in step 406 or step 410. The server 124 can access pathology database 128B to determine one or more physical conditions that may occur in one or more locations determined at step 406 or step 410. As discussed in relation to FIG. 1C, the pathology database 128B can be a dynamic database that includes information related to various physical conditions, including medical information about a particular physical condition, such as which blood vessels, nerves, and muscles are affected by the condition; symptoms and causes associated with a condition; and anatomical images indicating changes in physiology accompanying the condition. Additionally, the server may access anatomical information such as X-rays, ultrasound, CT-scan, MM, nerve conduction studies, and other imaging resources that may help the server 124 to determine potential physical conditions for different locations. For example, the server 124 may determine that the swelling in the user's calf muscle can be caused by sports injury, deep vein thrombosis, or inflammation. The server 124 may further determine that the redness in the user's foot can be caused by an insect bite, inflammation, or sun burn, as just a few examples.

The server 124 may additionally determine that various locations of physical conditions are related to a single underlying physical condition. Moreover, the server 124 may further determine the nature of various physical conditions associated with various locations such as clinical signs or various anatomical parameters affected by a physical condition, for example, the affected muscle groups and nerves, size and color of the affected area, and/or the severity of the physical condition such as chronic/persistent, transient, etc. The nature of a physical condition can be later used by the server 124 to determine if a physical condition is curable by a medical device. In some implementations, the server 124 determines a physical condition associated with a location simply by comparison of symptoms.

Once the server 124 has identified a set of possible physical conditions that may occur at a particular location, the server 124 further assigns a probability of occurrence to various contender physical conditions identified above for each location. The probability of occurrence can be based on standard clinical assessment tests for a particular physical condition obtained from the pathology database 128B. The probability of occurrence may also be based on information from the user profile database 128A and/or information provided by a user in the user input 112, such as age, gender, medical history, etc. For example, if the user indicated, in the user input 112, that the user was running just before the start of "pain in the leg" then the swelling in user's calf muscle due to sports injury will be assigned a high probability of occurrence. Additionally, the server 124 may use the standard "Wells Score" test to determine the probability of occurrence of deep vein thrombosis. Similarly, the server 124 may determine the probability of occurrence of redness in the foot due to insect bite, inflammation, or sun burn. If the user indicated that just before the start of "pain in the leg" the user was running indoors, then the redness in the foot due to sun burn and insect bite may be assigned a low probability whereas inflammation due to running may be assigned a high probability of occurrence. The server 124 may additionally use several artificial intelligence algorithms to determine and assign probability of occurrence to a physical condition. Any suitable computational technique can be used to assign the probability of occurrence to the one or more physical conditions, including but not limited to nearest-neighbor rule, minimum distance classifier, cascade classifier, bayesian classifier, multilayer perception, radial basis function network, support vector networks.

At step 414, the server 124 determines a subset of physical conditions identified in step 412 for which the probability of occurrence is higher than a threshold and which can also be treated using an electrotherapy device present in the placement database 128C. In one embodiment, for each of the physical conditions identified in step 412, the server 124 checks if the probability of occurrence associated with that physical condition is greater than a predetermined threshold. For each of the physical conditions identified in step 412, the server 124 further determines if a particular condition can be treated using a medical device. With this analysis, the server 124 can create a subset of physical conditions for which the probability of occurrence is higher than a threshold and can be treated using an electrotherapy device. In some cases, the electrotherapy device may not treat the physical condition but alleviates or relieves the symptoms of the physical condition.

At step 416, the server analyzes the set of physical conditions identified in step 412. If the server 124 determines that none of the physical conditions identified in step 412 have a probability of occurrence higher than a threshold and can be treated using an electrotherapy device, then the method moves to step 417, in which the server 124 reports back to the user that the physical condition cannot be identified. The method 400 then ends at step 418.

If, on the other hand, the server 124 determines that, for one or more physical conditions identified at step 412, the probability of occurrence is higher than the threshold and can be treated using an electrotherapy device, then the method proceeds to step 415, in which the server 124 determines an appropriate electrotherapy device to treat the physical condition. For example, based on the analysis performed at step 414, the server 124 may determine that the swelling in the user's calf muscle is due to sports injury and redness in the user's foot is caused by inflammation, and that both of the physical conditions can be treated by using several medical devices such as an Electronic Muscle Stimulator (EMS) device or a Transcutaneous Electrical Nerve Stimulation (TENS) device. In the next several steps, the server 124 will then determine an appropriate electrotherapy device to treat the one or more physical conditions identified in step 414.

The threshold may be a predetermined threshold (for example, a threshold decided by medical practitioners, radiologists, or another medical professional) or may be a dynamically determined threshold indicative of the minimum probability of a physical condition that warrants medical attention. In some implementations, the server 124 selects the physical condition with the highest probability of occurrence without comparing it to a threshold. In order to determine the set of electrotherapy devices, the server 124 may use information from the placement database 128C such as but not limited to product specifications, electrode placements guides, therapies offered by an electrotherapy device, and clinical recommendations. The server 124 may iterate this step for each member of the subset of physical conditions associated with each region of interest and thus determines a comprehensive list of medical devices that can treat, alleviate, or cure those physical conditions.

At step 415, the server 124 determines appropriate devices to treat the physical conditions. As described above, the physical condition may either be identified by the server 124 (for example, at step 412 and step 414) or specified by the user in the user input 112 in step 411. From the list of medical devices determined in step 414, the server 124 can use various optimization algorithms, such as simplex, combinatorial, etc., to determine an appropriate medical device to treat a physical condition. The server 124 may use information present in the user input 112, user profile database 128A, pathology database 128B, and the placement database 128C for optimization algorithms. Various constraints for optimization can be based on user preferences in the user input 112 such as but not limited to cost, vendor, geographical location, and previous and current medical conditions. Several other constraints may include information about medical devices such as current, frequency, amplitude, safety, ease of operation, energy transfer mechanisms, vendor support, and customer reviews. The server 124 may also include information about the physical conditions from the pathology database 128B (such as, for example, information about involved muscle groups or nerves and severity of the condition) to determine an appropriate device to treat a physical condition. The server 124 may prioritize the medical devices based on the results of optimization algorithms giving highest priority to the most appropriate medical device and the lowest priority to the least optimal device. In some implementations, the server 124 applies various optimization techniques to determine a closest matching electrotherapy device that meets different criteria based on user preferences.

The method next proceeds to step 420, in which the server 124 analyzes the user input 112 to determine if the user has identified a user-preferred electrotherapy device to treat a physical condition. If the user did not indicate a preferred electrotherapy device, the method proceeds to step 422, in which the server provides guidance for the appropriate electrotherapy device identified in step 415. In one example, the server 124 determines a placement position for each of the one or more energy-delivery nodes (such as electrodes) of the appropriate electrotherapy device identified in step 415 based on the characterized physical condition. The placement position can be selected from one of a plurality of node placement configurations stored in a node placement database. The method 400 can end after guidance is provided at step 422.

If the user did indicate a preferred electrotherapy device in the user input 112, then the method 400 proceeds to step 424, in which the server 124 extracts all the information related to that device from the placement database 128C. Furthermore, the server 124 can determine at step 424 if the treatment provided by the user-preferred electrotherapy device is comparable to the treatment provided by the appropriate device identified in step 415. In one embodiment, the server 124 uses various optimization techniques and mathematical algorithms similar to the ones used in step 415 to compare the therapeutic effect of the user-preferred electrotherapy device and the appropriate device identified in step 415. The server 124 may also take into account the time and efficacy of the treatment of two different devices.

If the server 124 determines at step 424 that the user-preferred device provides comparable treatment to the appropriate device, then the method moves to step 426, in which the server 124 provides guidance using the user-preferred electrotherapy device. In one example, the guidance includes a placement position for each of the one or more energy-delivery nodes (such as electrodes) of the user-preferred electrotherapy device based on the characterized physical condition, where the placement position is selected from a plurality of node placement configurations corresponding to the preferred electrotherapy device. The method 400 can end after guidance is provided at step 426.

If, however, the appropriate device identified in step 415 is better suited to treat the particular physical condition identified, then the method 400 moves to step 428. At step 428, the server 124 provides guidance using the user-preferred electrotherapy device in addition to the guidance using the appropriate electrotherapy device identified in step 415. In one embodiment example, the guidance includes a placement position for each of the one or more energy-delivery nodes (such as electrodes) of the user-preferred electrotherapy device and the appropriate electrotherapy device identified in step 415, where the placement positions are determined based on the characterized physical condition. The placement positions can be selected from a plurality of node placement configurations stored in a node placement database, for example. The node placement database can store a plurality of node or electrode configurations corresponding to the preferred electrotherapy device and/or the appropriate electrotherapy device. The method 400 can end after guidance is provided at step 428.

The methods used by the server 124 for determining a treatment plan and for providing a response to the user using either the user-preferred electrotherapy device or an appropriate device, as determined by the server 124 in the steps above, are similar to the methods discussed with reference to step 308 and step 310 of FIG. 3. In some other implementations, the server 124 only provides guidance for the appropriate device identified in step 415, and does not include guidance for the user-preferred device.

Figure 5:
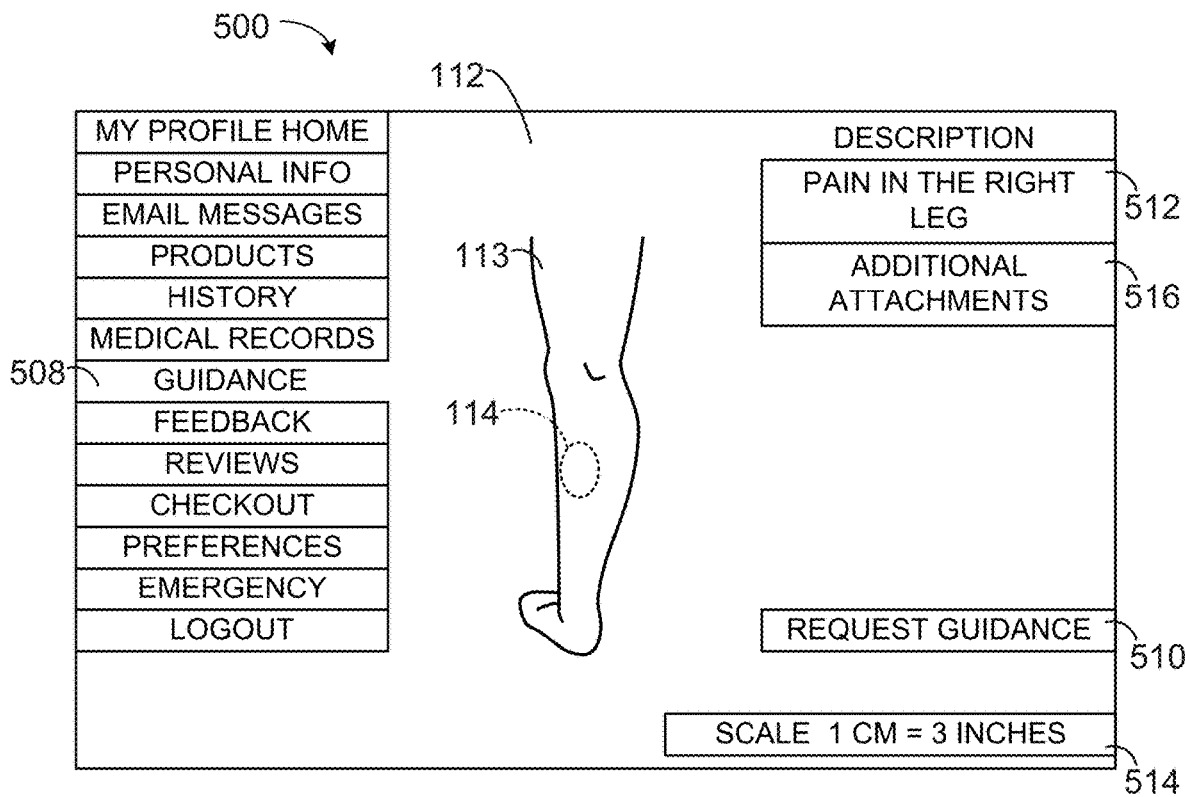
FIG. 5 is a diagram of a user interface according to one embodiment.

FIG. 5 is a diagram of a user interface 500 according to one embodiment of the present disclosure. The graphical user interface (GUI) 500 illustrated in FIG. 5 can be used to request guidance on the treatment of a physical condition. For example, the graphical user interface 500 can be implemented as a user interface of a user device 102, such as user interface 106 described above with reference to FIGS. 1B and 1C. Graphical user interface 500 may include several options to interact with the server 124. For example, the user may use a "PERSONAL INFO" option to input and store personal information including height, weight, age, gender, address, or the like. The "PERSONAL INFO" option may also store information about user activities such as athletic or other physical activity that may result into various physical conditions. The user may access e-mail messages generated by the system using an "EMAIL MESSAGES" option. The user may also send emails, such as emails to the system, using this option. In some implementations, a user may access the user's emails from any device connected to the network 116.

The graphical user interface 500 can include other features and options. For example, a "PRODUCTS" option can be used to store information about medical device products owned by the user. This option may also allow a user to compare a particular product to other products and to make a decision as to which product is most suitable for the user. If a user likes a product, the user can select and add that product into a virtual shopping cart for later purchase. This option may also display promotional information that may be tailored to the user's physical condition as provided in the user input requests. A "HISTORY" option stores recent history of a user's interaction with the system. For example, the "HISTORY" tab may provide access to a record of past guidance received by the user, prior diagnoses, and previous purchases, for future reference, analysis, or diagnosis.

A "MEDICAL RECORDS" option can allow a user to access and maintain the user's medical history. The medical history can include various forms of information, for example records of previous physical conditions, X-rays, MRI images, and CT scans of body parts. The system can be configured to take appropriate data security measures to protect user's medical records from unauthorized access. A "FEEDBACK" option can allow a user to provide feedback on the user's interaction with the system. For example, a user can provide feedback on the previous guidance the user received or may provide feedback on a particular product the user bought recently. Through this option, the user may also provide answers to the server's clarifying questions on the user input. A user may also provide an update or progress report on the treatment of a physical condition so that the computerized system 100 can determine whether prior guidance was effective or followed and the system may provide subsequent guidance.

Using a "REVIEWS" option, a user can see and review the user's experience or other users' experiences with a particular device or a therapy. A "CHECKOUT" option can allow a user to browse and buy a particular device or product from a particular vendor. A user may also keep a wish list of products that the user would like to buy in the future. This option may also securely store a user's financial information. A "PREFERENCES" option can allow a user to express preferences, such as but not limited to preferences for specific vendors, cost, products, therapy, and mode of communication. For example, a user may instruct the server 124 that receiving a response in an email is preferable. A user may also instruct a server to limit the guidance to recommendations based on user-owned or user-preferred devices. An "EMERGENCY" option can allow a user to access information about local doctors, for example, in case of an emergency. A "LOGOUT" option can allow a user to securely logout of the guidance application.

An example implementation of a "GUIDANCE" option 508 is illustrated in FIG. 5 and will now be described in greater detail. The "GUIDANCE" option can be used to send user input 112 and to request guidance to treat a physical condition. As described above with reference to FIG. 1, a user can send an image or video 113 of the user's body part indicating the location 114 of a physical condition. In some implementations, a user does not indicate the location of a physical condition and the server 124 determines the location and nature of a physical condition for the user. A user may provide additional description 512 of the physical condition for which the user is requesting guidance. For example, a user may write "pain in the right leg." In one non-limiting example, the user writes "pain in the right leg" using a touch screen feature of the graphical user interface 500. In another example, the user may use a voice-to-text feature of the user device 102 to add information describing the physical condition. For example, the user may input additional description 512 by speaking the words "pain in the right leg" using a voice-to-text functionality included in the graphical user interface 500. In both examples, the additional user input may appear in the graphical user interface 500 as the text "PAIN IN THE RIGHT LEG" in the additional description 512 section of the graphical user interface 500.

In some implementations, a user can add a scale 514 of the image to accurately indicate the location 114 of the physical condition on the user's actual body part. A user may also describe the context of the physical condition such as describing how and when the user started experiencing pain. Additionally, a user may include additional information as attachments 516 to the first media 113 which the user thinks may be useful for the analysis of the physical condition. For example, the additional attachments 516 can be any additional image or video. In some embodiments, the additional attachments 516 include CT scans, X-rays, MRI images, or the like. Once the user has entered all of the information the user wishes to send to the server 124, the user can request guidance on the treatment of a physical condition by initiating a "REQUEST GUIDANCE" option 510. In some embodiments, the user initiates the "REQUEST GUIDANCE" option 510 by pressing a button or touchscreen feature associated with the "REQUEST GUIDANCE" option 510 on the graphical user interface 500.

Figure 6:
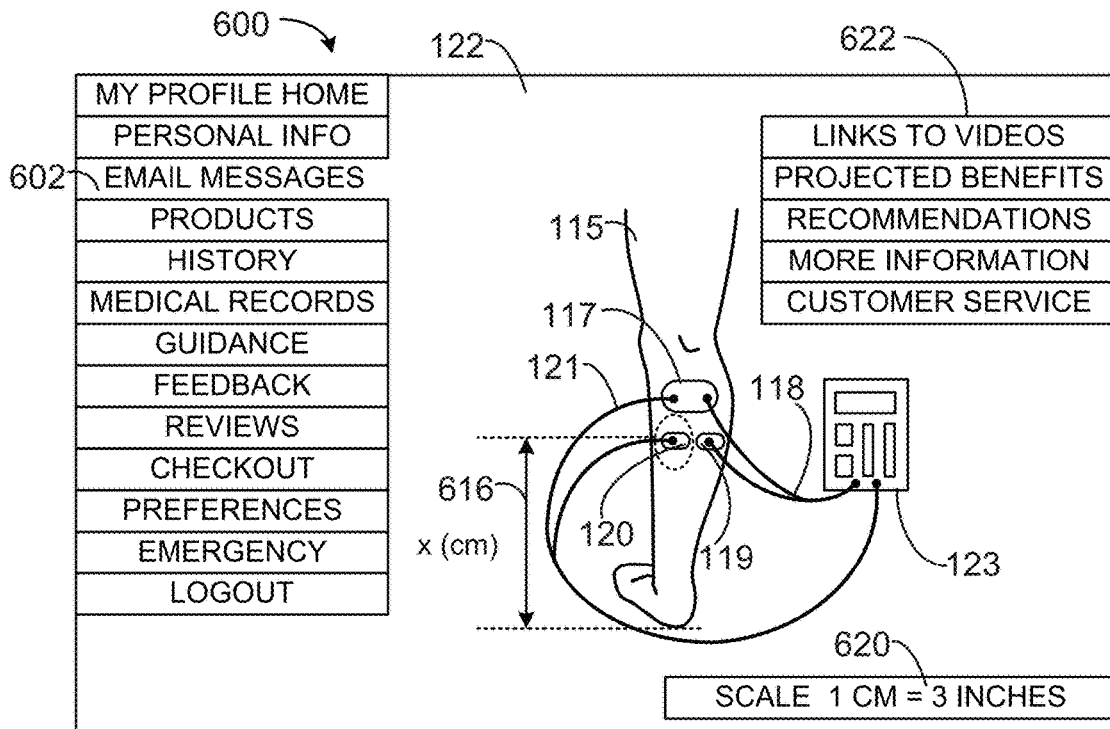
FIG. 6 is a diagram of a user interface according to another embodiment.

FIG. 6 is a diagram of a user interface 600 according to another embodiment of the present disclosure. The graphical user interface (GUI) 600 illustrated in FIG. 6 can be used by a user to receive guidance on the treatment of a physical condition. In one example, the user uses the graphical interface 600 to receive a guidance response 122 providing guidance to the user on use of an electrotherapy device to treat a physical condition. The graphical user interface 600 may be implemented as a user interface of a user device 102, such as user interface 106 described above with reference to FIGS. 1B and 1C. Alternatively, the graphical user interface 600 may be implemented on an interface associated with the server 124. In some implementations, a user uses separate graphical use interfaces to send a request for guidance (for example, graphical user interface 500) and to receive a response from the server 124 (for example, graphical user interface 600). The graphical user interfaces 500 and 600 may reside on separate user devices.

The guidance response 122 provided on graphical user interface 600 may be provided as an e-mail, a text message, as a link in the user profile, or by any suitable communication means. As part of a response from the server 124, a user may receive recommendations on usage, purchasing related parts, device settings, electrode sizes, etc. of one or more suitable electrotherapy devices that may help the user to treat the physical condition. The suitable device may be a preferred user device and/or a device determined by the server 124 that may be appropriate to treat a physical condition.

As described above with reference to step 310 of FIG. 3, a user may receive guidance in the form of placement positions of one or more electrodes of an appropriate electrotherapy device to treat a physical condition in response to the user input 112. The placement positions may be superimposed on second media 115. In the example illustrated in FIG. 6, the second media includes an image of the user's right leg. Alternatively, the guidance response 122 may include software instructions to annotate the first media 113 (such as an image or video) provided in the user input request. In some cases where the user may have a preferred device, the guidance response for treating the physical condition using the appropriate device may be included in addition to a guidance response using the user-preferred device.

In addition to placement positions, a guidance response 122 may include a distance 616 from one of the features (for example the base of the user's foot in the image) of the media for each of the placement positions 117, 119, and 120. The guidance response 122 may also include a measurement scale 620 which can be used by the user to translate the distance 616 provided in the guidance response 122 into actual distances relative to the user's body part. As described above with reference to FIGS. 4A and 4B, the server 124 may calculate the scale 620 from the mathematical model of the user's body part and user profile database 128A. The server 124 may also determine the scale 620 from the scale 514 provided by the user as described above with reference to FIG. 5.

In addition to the above-described customized guidance, the guidance response 122 may also include several other options 622 that the server 124 has determined may be useful to guide the user in implementing the therapy. For example, the graphical user interface 600 providing the guidance response 122 may include a "LINKS TO ILLUSTRATIVE VIDEOS" section that further includes lists of videos that are helpful to the user to understand the therapy and may visually describe, in a step-by-step manner, how to use an electrotherapy device and how to place its electrodes on the placement positions indicated in the guidance response 122. This option may also include enhanced and interactive instructions for using the device with guided flowcharts. Other useful videos may be related to vendor websites or links to other therapies, in addition to the suggested electrotherapy, which a user can use to alleviate the physical condition such as links to videos on yoga or other exercises.

Additional useful options can be provided in a "PROJECTED BENEFITS" section of the graphical user interface 600. This section can allow a user to view customized charts and a description of the projected benefits to a user on using the instructed therapy. This option may also include simplified animations to educate a user of the projected benefits of the recommended therapy. Similarly, the guidance response 122 may also include an option indicated in a "RECOMMENDATIONS" section of the graphical user interface 600 that describes a recommended treatment plan detailing how and when to use the electrotherapy device, duration of the therapy, recommended settings of the electrotherapy device, etc. This option may further include detailed information and safety instructions for the recommended electrotherapy device.

The guidance response 122 may also include an option labeled "MORE ABOUT PHYSICAL CONDITION" or "MORE INFORMATION" that describes the selected physical condition in detail. For example, it may describe the symptoms and causes of a particular physical condition. This option may also have customized 3D anatomical models and an educational presentation on the user's physiology to further elaborate medical reasons for the physical condition. The guidance response 122 may also include a "CUSTOMER SERVICE" option that includes links to call or contact customer service in case of any need for further support or questions.

In some cases, the user may have a preference for a particular electrotherapy device. The preference may be based on a device the user already owns, cost considerations, availability, vendor preferences, or other factors. In such cases, the system may provide recommendations that are constrained to use the particular preferred device or devices that fall within the preference. Because such recommendations may be constrained to a limited set of electrotherapy devices, the guidance provided may not reflect the optimal treatment for the condition. This may be the case, for example, if the preferred devices are limited in their ability to treat the identified physical condition. In such cases, the system may provide multiple recommendations, including at least one recommendation based on guidance related to the preferred electrotherapy device, and a second recommendation based on a determination of a more appropriate electrotherapy device for the condition.

Figure 7:
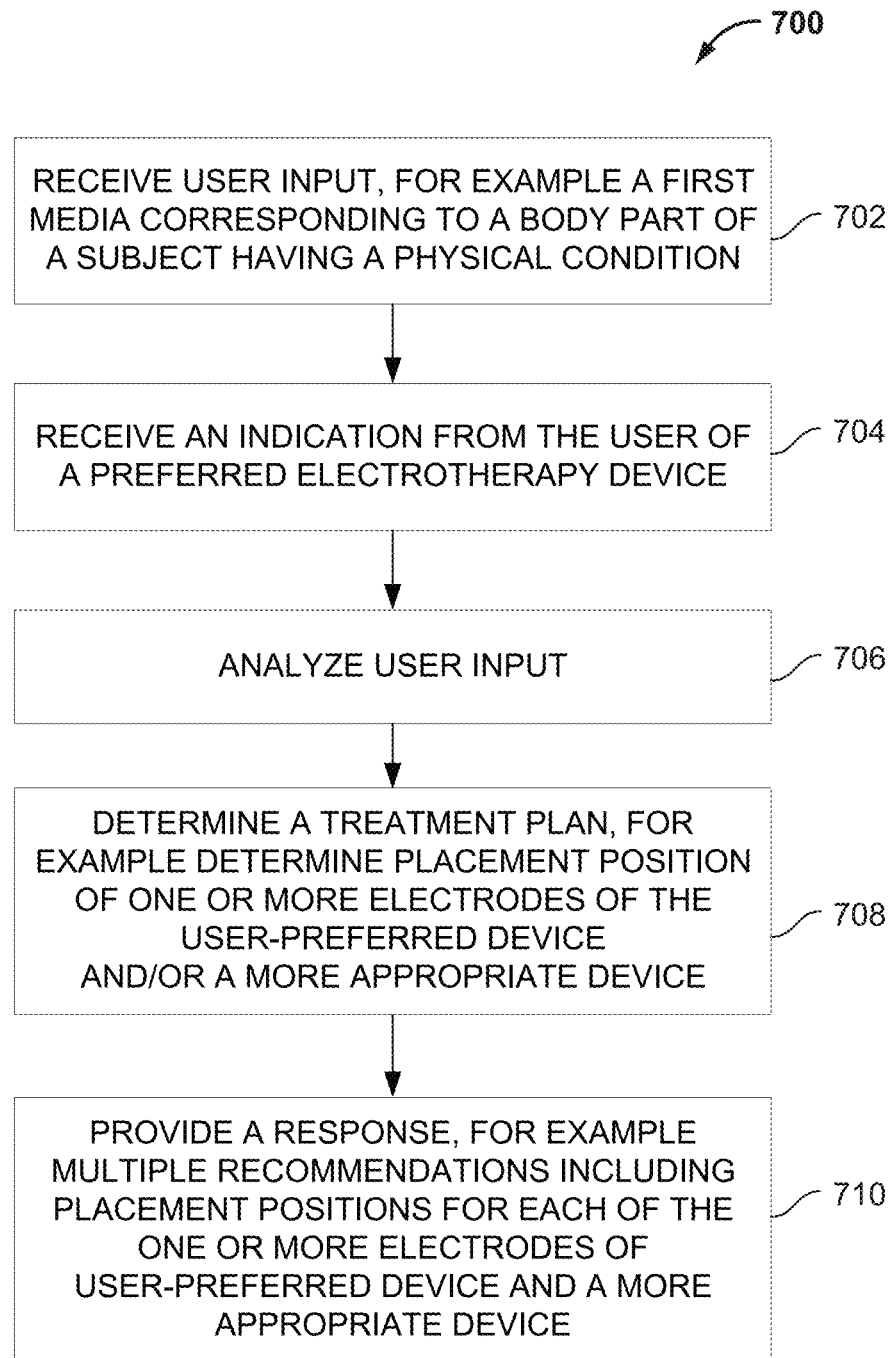
FIG. 7 is a flowchart illustrating a method for providing guidance on use of a user-preferred energy-based therapeutic device to treat a physical condition according to one embodiment.

FIG. 7 is a flowchart illustrating a method 700 that may be implemented by the system 100 according to one embodiment of the present disclosure. The method 700 can provide guidance on use of a preferred electrotherapy device for treating a physical condition. The method 700 is described with reference to a client-server implementation illustrated in FIG. 1B. However, the method 700 may be implemented using any of the system implementations described herein. In addition, the steps of the method 700 may be performed simultaneously, reversed, or some steps may be omitted.

The method 700 can include the steps of a user device 102 sending a user input 112 to the server 124 to request guidance to treat a physical condition using a preferred electrotherapy device. As described above with reference to FIG. 3, some steps may precede the start of the method 700. For example, prior to step 702 in which a user input is sent to the server 124, the user may authenticate with the server 124 by inputting a username and password (or providing other identification information) via user interface 106. The method may then begin at step 702, in which the user selects a "My Profile Home" option, for example the "My Profile Home" option included in the graphical user interface 500 of FIG. 5. At step 702, the computerized system 100 may receive user input for a first media 113 corresponding to a body part of a subject having a physical condition, similar to the example implementations described with reference to step 302 of FIG. 3. In some cases, step 702 of method 700 is substantially similar to step 302 of FIG. 3 described above.

The method 700 next moves to step 704, in which the server 124 (or any suitable processing circuitry in the system 100) receives an indication of a preferred electrotherapy device from the user. The preferred electrotherapy device may be a device owned or easily accessible to the user. The preferred electrotherapy device may also be a device from a preferred vendor. It may also be based on information from the user profile database 128A. The user may indicate the user's device preferences along with the user input 112 as described above with reference to FIG. 5.

The method 700 then proceeds to step 706, in which the server 124 analyzes the user input received at steps 702 and 704. In some cases, the step 706 of method 700 is substantially similar to step 304 of method 300. The step 706 of method 700 may be substantially similar to the method 400 described with reference to FIGS. 4A and 4B.

The method 700 next proceeds to step 708, in which the server 124 determines a treatment plan for the user. In some case, the step 708 may be substantially similar to step 308 described with reference to FIG. 3. Similar to step 308 of method 300, the server 124 may determine a treatment plan for the physical condition in step 708. The treatment plan may be determined using a user-preferred electrotherapy device. In some cases, due to limitations of the preferred device, the treatment plan may not be optimal. In such cases the server 124 may additionally determine a treatment plan using a more appropriate electrotherapy device. The appropriate device may be better suited to treat the physical condition than the user-preferred device. For example, if the user-preferred device has only two electrodes and the server 124 determines that the physical condition may be better treated using a device including four electrodes, then the server 124 may determine a treatment plan using the better suited device including four electrodes in addition to the treatment plan using the user-preferred device including two electrodes.

Moving next to step 710, the server 124 provides a response to the user. The step 710 may be substantially similar to step 310 described above with reference to FIG. 3. Similar to step 310 of method 300, the server 124 may provide guidance in step 710 to treat the indicated physical condition. The guidance can be in the form of providing recommendations to use the user-preferred device. In a case where the user-preferred device is limited in its ability to treat the identified physical condition, then the guidance may also include recommendations of a more appropriate device or more appropriate parts of the user-preferred device such as new electrodes. The guidance may include vendor-furnished incentives (for example, discounts) for the user to easily acquire new device or parts of an existing device. The method 700 ends following step 710.

Figure 8:
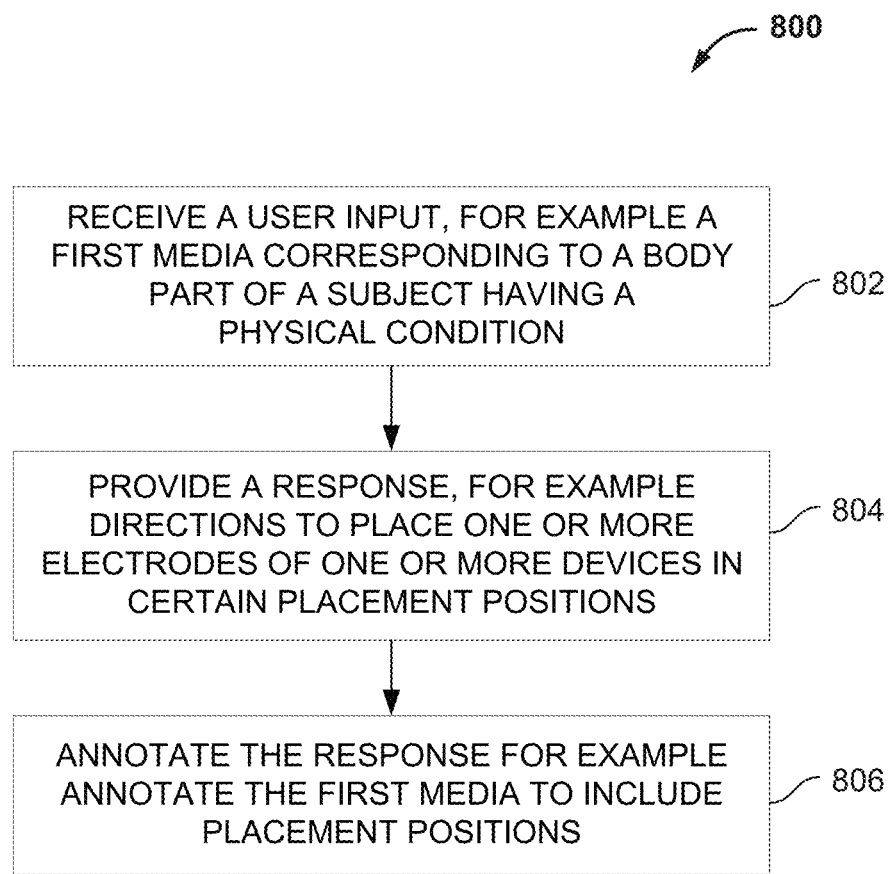
FIG. 8 is a flowchart illustrating a method for providing guidance on use of an energy-based therapeutic device to treat a physical condition according to still another embodiment.

FIG. 8 is a flowchart illustrating a method 800 that may be implemented by the system 100 according to another embodiment of the present disclosure. The method 800 can be implemented by the user device 102 (or another component of computerized system 100) to receive guidance on use of an electrotherapy device for treating a physical condition. The method 800 is described with reference to a client-server implementation illustrated in FIG. 1B. However, the method 800 may be implemented using any of the system implementations described herein. In addition, the steps of the method 800 may be performed simultaneously, reversed, or some steps may be omitted.

The method 800 can include the steps of a user device 102 sending a user input to the server 124 requesting guidance to treat a physical condition. In some cases, the step 802 of method 800 is substantially similar to step 302 described above with reference to FIG. 3. As described above with reference to FIG. 3, some steps may precede the start of the method 800. For example, prior to step 802 in which a user input is sent to the server 124, the user may authenticate with the server 124 by inputting a username and password (or providing other identification information) via user interface 106 (such as the graphical user interface 500 of FIG. 5). The method 800 may then begin at step 802, in which the user selects a "My Profile Home" option, for example the "My Profile Home" option included in the graphical user interface 500 of FIG. 5. At step 802, the computerized system 100 may receive user input for a first media 113 corresponding to a body part of a subject having a physical condition, similar to the example implementations described with reference to step 302 of FIG. 3. In some cases, step 802 of method 800 is substantially similar to step 302 of FIG. 3 described above.

Moving next to step 804, the server 124 provides a response to the user. The step 804 may be substantially similar to step 310 described above with reference to FIG. 3. Similar to step 310 of method 300, the server 124 may provide guidance to the user in step 804. In one example, the server 124 provides guidance in the form of directions to place one or more electrodes of one or more devices in certain placement positions.

Moving next to step 806, the user device 102 annotates the received response on the user input 112. For example, the processor 104 included in the user device 102 may use the directions provided in the response to overlay the placement positions on the first media 113 that was previously stored on the user device 102. The user device 102 may include a media projecting device and may project the placement positions 117, 119, and 120 directly on the user's actual body part using one or more augmented reality algorithms.

Those of skill will recognize that the various illustrative logical blocks, modules, circuits, and algorithm steps described in connection with the embodiments disclosed herein, including with reference to the electrotherapy devices and systems described herein, for example, may be implemented as electronic hardware, software stored on a computer readable medium and executable by a processor, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. For example, various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Software associated with such modules may reside in RAM memory, flash memory, ROM memory, EPROM memory, EEPROM memory, registers, a hard disk, a removable disk, a CD-ROM, or any other suitable form of storage medium known in the art. An exemplary storage medium is coupled to the processor such the processor can read information from, and write information to, the storage medium. In the alternative, the storage medium may be integral to the processor. The processor and the storage medium may reside in an ASIC. For example, in one embodiment, a server 124 described with reference to FIG. 1B includes a controller (not shown), and the controller includes a processor 126. In one embodiment, the processor 126 is a placement-position processor configured to process a user input 112 to determine a placement position for each of one or more energy-delivery nodes of an energy-based therapeutic device.

It is to be understood that the foregoing description is merely illustrative, and is not to be limited to the details given herein. While several embodiments have been provided in the present disclosure, it should be understood that the disclosed systems, devices, and methods and their components may be embodied in any other specific forms without departing from the scope of the disclosure. For example, the systems, devices, and methods disclosed herein, while shown for use in electrotherapy devices, can be applied to systems, devices, and methods to be used for other non-invasive energy-based therapeutic devices used to treat physical conditions. In particular, the systems and methods described above can be applied to provide guidance on the placement of one or more energy-delivery nodes for any energy-based therapeutic device. For example, the systems and methods described above can be applied to hot or cold pain relieving gels, ultrasound devices, laser-based devices, shockwave therapy devices, cryotherapy devices, and the like, with respect to the treatment of one or more of any number of physical conditions and therapeutic purposes, including, for example, pain management, orthopedic rehabilitation, physical therapy, fitness and sport performance enhancement, and the like.

Variations and modifications will occur to those of skill in the art after reviewing this disclosure, where disclosed features may be implemented in any combination and sub-combinations (including multiple dependent combinations and subcombinations), with one or more other features described herein. The various features described or illustrated above, including any components thereof, may be combined or integrated in other devices, systems or methods; moreover, certain features may be omitted or not implemented. It will also be appreciated by those of skill in the art that parts described with reference to one embodiment are interchangeable with other embodiments; one or more parts from a depicted embodiment can be included with other depicted embodiments in any combination. For example, any of the various components described herein and/or depicted in the Figures may be combined, interchanged, or excluded from other embodiments. Thus, while the present disclosure has described certain practical embodiments, it is to be understood that the invention is not limited to the disclosed embodiments, but, on the contrary, is intended to cover various modifications and equivalent arrangements included within the scope of the appended claims, and equivalents thereof.

What is claimed is:

1. A system for determining placement positions for energy-delivery nodes of an energy-based therapeutic device, the system comprising:
   an imaging device configured to generate a first media corresponding to a body part of a subject;
   a processor configured to:
      receive, as a first user input, the first media corresponding to the body part of the subject;
      receive, as a second input, an indication of a preferred energy-based therapeutic device; and
      provide a response, as a first output, by annotating the first media to include an indication of one or more placement positions at which one or more of the energy-delivery nodes of the energy-based therapeutic device are to be placed on the body part, wherein the processor is further configured to determine the one or more placement positions based on the first input, the second input, and a node placement database configured to store a plurality of node placement configurations, each of the plurality of node placement configurations providing placement positions for energy nodes for each of a plurality of energy-based therapeutic devices.

2. The system of claim 1, wherein the processor is further configured to analyze the first media to determine a physical condition to be treated with an energy-based therapy.

3. The system of claim 1, wherein the first media comprises an image or a video.

4. The system of claim 1, wherein the processor is further configured to:
   receive additional information relating to the physical condition or the subject; and
   analyze the additional information to characterize a physical condition of the body part.

5. The system of claim 4, wherein the additional information comprises at least one of a history of the physical condition, a symptom of the physical condition, demographic information about the subject, and a health history of the subject.

6. The system of claim 4, further comprising a memory configured to store a patient database, and wherein the processor is further configured to receive additional information from the patient database.

7. The system of claim 1, wherein the energy-based device is one of an electrotherapy device, a laser-based device, an ultrasound device, a shockwave therapy device, a temperature-based therapy device, and combinations thereof.

8. A method comprising:
   receiving from an imaging device, as a first user input, a first media corresponding to the body part of a subject;
   receiving, as a second user input, an indication of a preferred energy-based therapeutic device; and
   providing a response, as a first output, by annotating the first media to include an indication of one or more placement positions at which one or more energy-delivery nodes of an energy-based therapeutic device are to be placed on the body part, wherein the one or more placement positions are determined based on the first input, the second input, and a node placement database configured to store a plurality of node placement configurations, each of the plurality of node placement configurations providing placement positions for energy nodes for each of a plurality of energy-based therapeutic devices.

9. The method of claim 8, further comprising analyzing the first media to determine a physical condition to be treated with an energy-based therapy.

10. The method of claim 8, wherein the first media comprises an image or a video.

11. The method of claim 8, further comprising:
    receiving additional information relating to the physical condition or the subject; and
    analyzing the additional information to characterize a physical condition of the body part.

12. The method of claim 11, wherein the additional information comprises at least one of a history of the physical condition, a symptom of the physical condition, demographic information about the subject, and a health history of the subject.

13. The method of claim 11, further comprising accessing a patient database, and wherein the processor is further configured to receive additional information from the patient database.

14. The method of claim 8, wherein the energy-based device is one of an electrotherapy device, a laser-based device, an ultrasound device, a shockwave therapy device, a temperature-based therapy device, and combinations thereof.

* * * * *